United States Patent [19]

Heymes et al.

[11] Patent Number: 5,057,512
[45] Date of Patent: * Oct. 15, 1991

[54] 3-AMINO-2-OXO-AZETIDINE-1-SULFONIC ACIDS

[75] Inventors: Rene Heymes, Vesoul; Alain Bonnet, Livry-Gargan, both of France

[73] Assignee: Roussel Uclaf, Paris, France

[ * ] Notice: The portion of the term of this patent subsequent to Feb. 13, 2007 has been disclaimed.

[21] Appl. No.: 319,477

[22] Filed: Mar. 3, 1989

Related U.S. Application Data

[60] Division of Ser. No. 68,141, Jun. 29, 1987, Pat. No. 4,900,728, which is a continuation of Ser. No. 855,161, Apr. 23, 1986, abandoned, which is a continuation of Ser. No. 588,139, Mar. 9, 1984, abandoned, which is a continuation-in-part of Ser. No. 436,526, Oct. 25, 1982, abandoned.

[30] Foreign Application Priority Data

Oct. 23, 1981 [FR] France .................... 8119942
Jan. 19, 1984 [FR] France .................... 8400799

[51] Int. Cl.$^5$ .................. A61K 31/425; C07D 205/85; C07D 417/12
[52] U.S. Cl. ..................... 514/210; 540/355
[58] Field of Search ............ 514/210; 540/355

[56] References Cited

U.S. PATENT DOCUMENTS 4,533,495  8/1985  Yoshioka ................... 540/355

Primary Examiner—Mark L. Berch
Attorney, Agent, or Firm—Bierman and Muserlain

[57] ABSTRACT

Novel syn isomers of reacemates and optical isomers of 3-amino-2-oxo-azetidine-1-sulfonic acids of the formula

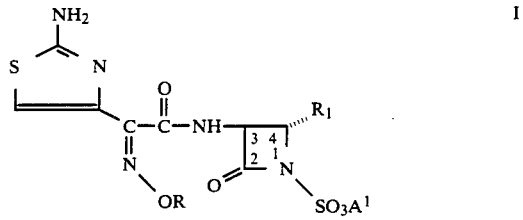

wherein R is difluoromethyl, $R_1$ is —$(CH_2)_n$—X, n is an integer from 1 to 4, X is selected from the group consisting of halogen, —CN, —$OR_1'$, —$SR_1''$, azido, thiocyanate, isothiocyanate, and

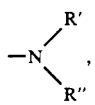

$R_1'$ is selected from the group consisting of hydrogen and alkyl of 1 to 4 carbon atoms, $R_1''$ is selected from the group consisting of hydrogen, alkyl of 1 to 4 carbon atoms and a heterocycle and R' and R" are individually selected from the group consisting of hydrogen and alkyl of 1 to 4 carbon atoms and taken together with the nitrogen to which they are attached form a heterocycle and $A^1$ is selected from the group consisting of hydrogen, and metal cations and their nontoxic, pharmaceutically acceptable acid addition salts, the wavy line indicating the cis form, trans form or cis trans forms having antibiotic properties.

12 Claims, No Drawings

5,057,512

3-AMINO-2-OXO-AZETIDINE-1-SULFONIC ACIDS

PRIOR APPLICATION

This application is a divisional of U.S. patent application Ser. No. 068,141 filed June 29, 1987, U.S. Pat. No. 4,900,728 which is a continuation of U.S. patent application Ser. No. 855,161 filed Apr. 23, 1986, which is a continuation of U.S. patent application Ser. No. 588,139 filed Mar. 9, 1984, which in turn is a continuation-in-part of copending, commonly assigned U.S. patent application Ser. No. 436,526 filed Oct. 25, 1982, now abandoned.

STATE OF THE ART

British Patent No. 2,071,650, U.S. Pat. No. 4,288,364 and French Patents No. 2,313,362 and No. 2,361,885, U.S. Pat. No. 4,085,100 and European Patent No. 21,678 describe related compounds.

OBJECTS OF THE INVENTION

It is an object of the invention to provide the novel compounds of formula I and their non-toxic, pharmaceutically acceptable acid addition salts and their preparation.

It is another object of the invention to provide novel antibiotic compositions and to combat bacterial infections in warm-blooded animals.

These and other objects and advantages of the invention will become obvious from the following detailed description.

THE INVENTION

The novel compounds of the invention are selected from the group consisting of syn isomers of racemates and optical isomers of 3-amino-2-oxo-azetidine-1-sulfonic acids of the formula

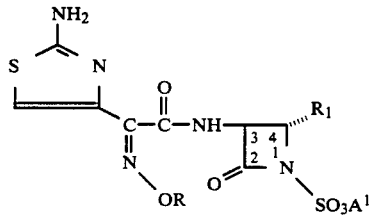

wherein R is selected from the group consisting of hydrogen linear or branched optionally substituted alkyl of 1 to 12 carbon atoms and optionally substituted alkenyl and alkynyl of 2 to 12 carbon atoms, $R_1$ is $-(CH_2)_n-X$, n is an integer from 1 to 4, X is selected from the group consisting of halogen, $-CN$, $-OR_1'$, $-SR_1''$, azido, thiocyanate, isothiocyanate, and

$R_1'$ is selected from the group consisting of hydrogen and alkyl of 1 to 4 carbon atoms, $R_1''$ is selected from the group consisting of hydrogen, alkyl of 1 to 4 carbon atoms and a heterocycle and R' and R" are individually selected from the group consisting of hydrogen and alkyl of 1 to 4 carbon atoms and taken together with the nitrogen to which they are attached form a heterocycle and $A^1$ is selected from the group consisting of hydrogen, and metal cations and thier nontoxic, pharmaceutically acceptable acid addition salts, the wavy line indicating the cis form, trans form or cis trans forms.

Examples of R are a) alkyl such as methyl, ethyl, propyl, isopropyl, butyl, sec-butyl, tert.-butyl, pentyl, iso-pentyl, sec-pentyl, tert-pentyl, neo-pentyl, hexyl, iso-hexyl, sec-hexyl, tert-hexyl, heptyl, octyl, decyl, undecyl and dodecyl, b) alkenyl such as vinyl, allyl, 1-propenyl, butenyl, pentenyl and hexenyl and c) alkynyl such as ethynyl, propargyl and butynyl. The groups a) to c) may be substituted by at least one member of the group consisting of carboxy optionally salified or esterified, alkoxycarbonyl of 2 to 7 carbon atoms such as methoxycarbonyl and ethoxycarbonyl, cyano, carbamoyl, dimethylcarbamoyl, amino, dialkylamino such as dimethylamino, diethylamino, alkylamino such as methylamino, halogen such as chlorine, bromine or iodine, alkoxy of 1 to 7 carbon atoms such as methoxy, ethoxy and propoxy, alkylthio of 1 to 7 carbon atoms such as methylthio and ethylthio, aryl such as phenyl, or aryl heterocyclic such as tetrazolyl and pyridinyl, arylthio such as phenylthio optionally substituted and aryl heterocyclic-thio such as tetrazolythio and thiadiazolythio optionally substituted with an alkyl of 1 to 7 carbon atoms such as methyl.

Examples of R are hydrogen, methyl, carboxyethyl optionally esterified or salified, 1-carboxy-1-methyl-ethyl optionally esterified or salified, and 2-amino ethyl and difluoromethyl.

Examples of $R_1$ are chloromethyl, chloroethyl, chloropropyl, 1-chloro-1-methyl-ethyl and chlorobutyl as well as the corresponding bromine, iodine or fluorine substituents in particular bromomethyl and fluoromethyl; cyanomethyl, cyanomethyl and the corresponding alkyls.

Examples of $R_1'$ and $R_1''$ are alkyl of 1 to 4 carbon atoms and especially methyl. $R_1''$ may also be a heterocycle such as 1,2,3-thiadiazolyl 1,2,5-thiadiazolyl 1,2,4-thiadiazolyl or 1,3,4-thiadiazolyl; 1H tetrazolyl; 1,3-thiazolyl; 1,2,3 or 1,2,4-triazolyl; 1,3,4-triazolyl; 1,2,3-oxadiazolyl; 1,2,4-oxadiazolyl; 1,2,5-oxadiazolyl; 1,3,4-oxadiazolyl, all optionally substituted by at least one member of the group consisting of methyl, ethyl, propyl, isopropyl, methoxy, ethoxy, propyloxy, isopropyloxy, amino, hydroxycarbonylmethyl, dimethylaminoethyl and diethylaminoethyl. Especially preferred are 1-methyl-tetrazolyl, 2-methyl-1,3,4-thiadiazolyl, 3-methyl-1,2,4-thiadiazolyl, 3-methoxy-1,2,4-thiadiazolyl, 1,3,4-thiadiazol-5-yl and more especially, 1-methyl-tetrazolyl radicals.

The

can be amino, dimethylamino, methylamino, ethylamino, diethylamino, piperidino, or morpholino.

The sulfo acid in position 1 as well as the carboxy which the radical R can contain can be salified. Examples are the salts of sodium, potassium, lithium, calcium, magnesium, and ammonium, the salts of organic bases such as trimethylamine, diethylamine, triethylamine, methylamine, propylamine, N,N-dimethyl-ethanolamine, tris (hydroxymethyl) aminomethane, ethanolamine, pyridine, picoline, dicyclohexylamine, N',N'- dibenzylethylenediamine, morpholine, benzylamine, procaine, lysine, arginine, histidine, N-methyl glucamine.

Examples of acids for the formation of non-toxic, pharmaceutically acceptable acid addition salts are organic acids such as acetic acid, trifluoroacetic acid, maleic acid, tartaric acid, methanesulfonic acid, benzenesulfonic acid, p-toluene-sulfonic acid and mineral acids such as hydrochloric acid, hydrobromic acid, sulfuric acid and phosphoric acid. The products with the formula (I) can also be in the form of internal salts. The preferred products are the cis products.

More preferred are the syn isomers of products in the cis form of the formula

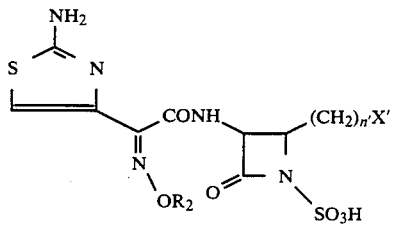

I' wherein $R_2$ is selected from the group consisting of hydrogen and linear or branched alkyl optionally substituted by at least one halogen, cyano, carboxyl or amino, n' is a whole number from 1 to 2 and X' is fluoro, thiocyanato or 2-pyri-dinylthiomethyl, in the racemic or optically active form, as well as the salts of the said compounds with bases or acids.

Also preferred are compounds of formula I' wherein n' is 1 and X' is fluoro and those wherein $R_2$ is hydrogen or methyl, difluoromethyl, carboxymethyl optionally salified or esterified, aminoethyl, cyanomethyl and 1-methyl-1-carboxy-ethyl optionally salified or esterified. Especially preferred are the racemates of the syn isomer of cis 4-fluoromethyl-3-[2-(2-amino-4-thiazolyl)-2-methoxy-imino-acetamido]-2-oxo-azetidine-1-sulfonic acid as well as of cis 4-fluoromethyl-3-[2-(2-amino-4-thiazolyl)-2-difluoromethoxy-imino-acetamido]-2-oxo-azetidine-1-sulfonic acid and their salts.

It is understood that the compounds of formula I can also exist in the tautomeric imine form of the formula

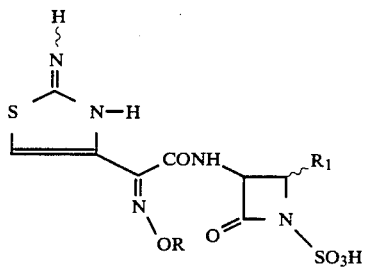

Iz

The lactam nucleus is numbered as follows

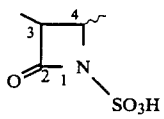

and the products designated cis are the compounds of the formula

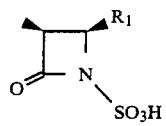

The trans compounds have the formula

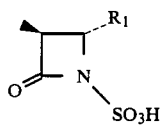

The novel process of the invention for the preparation of compounds of formula I comprises reacting a racemic or optically active compound of the formula

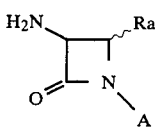

II wherein Ra is $R_1$ and $R_1$ has the above definition or Ra may be the protected functions of $R_1$ and A is hydrogen or sulfo with a compound of the formula

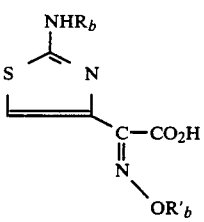

III wherein $R_b$ is selected from the group consisting of hydrogen and an amino protective group and $R_b'$ is a hydroxyl protective group or R of the above significance or protected R reactive groups to obtain a racemic mixture or an optical isomer of a compound of the formula

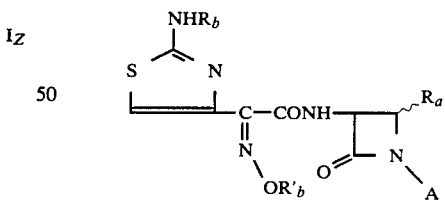

IV which if desired can be submitted to at least one of the following reactions in any desired order:

a) removal by hydrolysis, hydrogenolysis or by reaction with thiourea of the protective group or groups which $R_b$ and $R_b'$ represent or which $R_b'$ and $R_a$ can include.

b) Esterification or salification of the carboxy which $R_b'$ can include and salification of the sulfo radical.

c) Salification by an acid of any amino.

d) Sulfonation of the products in which A is hydrogen.

e) Resolution of the molecule so as to obtain an optically active product.

In the compounds of formula II, $R_a$ is usually $R_1$, but when $R_1$ is —$(CH_2)_n$—X, especially when X is —OH or —$NH_2$, it is preferred to protect the said groups with removable groups. Examples of amine protective groups are alkyl such as tert.-butyl or tert.-amyl and acyl groups of aliphatic, aromatic or heterocyclic carboxylic acids and carbamoyl.

Examples of lower alkanoyl groups are formyl, acetyl, propionyl, butyryl, isobutyryl, valeryl, isovaleryl, oxalyl, succinyl and pivaloyl, $R_b$ can also be lower alkoxy or cycloalkoxycarbonyl such as methoxycarbonyl, ethoxycarbonyl, propoxycarbonyl, 1-cyclopropylethoxycarbonyl, isopropyloxycarbonyl, butyloxycarbonyl, tert.-butyloxycarbonyl, pentyloxycarbonyl, hexyloxycarbonyl, benzoyl, toluolyl, naphthoyl, phthaloyl, mesyl, phenylacetyl and phenylpropionyl, or an aralkoxycarbonyl such as benzyloxycarbonyl.

The acyl groups may be substituted, for example, by chlorine, bromine, iodine or fluorine such as chloroacetyl, dichloroacetyl, trichloroacetyl, bromoacetyl or trifluoroacetyl. A lower aralkyl group such as benzyl, 4-methoxybenzyl or phenylethyl, trityl, 3,4-dimethoxybenzyl or benzhydryl may also be used. A haloalkyl such as trichloroethyl may also be used.

Other examples are chlorobenzoyl,p-nitrobenzoyl tert.-butylbenzoyl,phenoxyacetyl, caprylyl, n-decanoyl, acryloyl, or trichloroethoxycarbonyl. Also to be utilized are methylcarbamoyl, phenylcarbamoyl, naphthylcarbamoyl as well as the corresponding thiocarbamoyls. The above list is not limitative, since it is obvious that other amine protective groups, especially those known in the chemistry of the peptides, can equally be utilized.

The protective group for the hydroxyl radical can be an acyl group such as formyl, acetyl, chloroacetyl, bromoacetyl, dichloroacetyl, trichloroacetyl, trifluoroacetyl, methoxyacetyl, phenoxyacetyl, benzoyl, benzoylformyl and p-nitrobenzoyl. There can also be used ethoxycarbonyl, methoxycarbonyl, propoxycarbonyl, $\beta\beta\beta$-trichloroethoxycarbonyl, benzyloxycarbonyl, tert.-butoxycarbonyl, 1-cyclopropylethoxycarbonyl, tetrahydropyrannyl, tetrahydrothiopyranyl, methoxytetrahydropyranyl, trityl, benzyl, 4-methoxybenzyl benzhydryl, trichloroethyl, 1-methyl 1-methoxyethyl and phthaloyl.

Others acyls such as propionyl, butyryl, isobutyryl, valeryl, isovaleryl, oxalyl, succinyl and pivaloyl can also be used as well as phenylacetyl, phenylpropionyl, mesyl, chlorobenzoyl, paranitrobenzoyl, p-tertbutylbenzoyl, caprylyl, acryloyl,methylcarbamoyl, phenylcarbamoyl and naphthylcarbamoyl.

Naturally, the values of the substituents $R_b$, when these do not represent a hydrogen atom, as well as the values of the protective groups which $R_b'$ can possibly represent or include in particular when $R_b'$ includes an amine,can also be taken from the lists mentioned above.

In a mode of the process of the invention, the compound of formula II is reacted with a functional derivative of a compound of formula III. This functional derivative can for example be a halide, a symmetric or mixed anhydride, an amide or an activated ester.

An example of a mixed anhydride may be that formed with isobutyl chloroformate and that formed with pivaloyl chloride and the mixed carboxylic-sulfonic anhydrides formed for example, with p-toluene sulfonyl chloride. An example of an activated ester is the ester formed with 2,4-dinitrophenol and that formed with hydroxybenzothiazole. As example of an acid halide, there can be cited the chloride or bromide. There can also be used the acid azide or the acid amide. The anhydride can be formed in situ by the action with a N,N'-disubstitutedcarbodiimide, such as N,N-dicyclohexylcarbodiimide.

The acylation reaction is preferably carried out in an organic solvent such as methylene chloride. Other solvents such as tetrahydrofuran, chloroform or dimethylformamide can be used.

When an acid halide is used, and in a general way when a hydrogen halide is liberated in the reaction, it is preferable to carry out the reaction in the presence of a base such as sodium hydroxide, potassium hydroxide, carbonates and bicarbonates of sodium or potassium, sodium acetate, triethylamine, pyridine, morpholine or N-methylmorpholine. The reaction temperature is generally less than or equal to the ambient temperature. When $R_b$ is hydrogen, it is preferred to use a carboxylic-sulfonic mixed anhydride.

Depending on the values of $R_b$, $R_b'$ and Ra, the products of formula IV may or may not fall within the scope of formula I. The products of formula IV fall within the scope of formula I when $R_b$ is hydrogen, when $R_b'$ is not a protective group for hydroxyl or is not R including a protected function, and finally when $R_a$ is not $R_l$ in which a reactive function is protected and when A is not hydrogen.

In the other cases, the action on the product of formula IV of one or more hydrolysis or hydrogenolysis agents or of thiourea will eliminate $R_b$ when the latter is a protective radical of the amino, of eliminating $R_b'$ when the latter is a protective group of the hydroxyl, and of eliminating the other protective groups which $R_a$ and $R_b'$ can include.

The kind of reagents to be put in action in all these cases is well known to an expert in the subject. Examples of such reactions are given further on in the experimental part. There is given below a non-exhaustive list of the means which can be employed to eliminate the different groups.

The elimination of the group $R_b$ can be effected by acidic or basic hydrolysis or by utilizing hydrazine. It is preferred to use acid hydrolysis to eliminate optionally substituted alkoxy and cycloalkoxycarbonyl groups, such as tert-pentyloxycarbonyl or tert-.butyloxycarbonyl, optionally substituted aralkoxycarbonyls such as benzyloxycarbonyl, and trityl, benzhydryl, tert-.butyl or 4-methoxy-benzyl. The acid which is preferably used may be chosen from the group consisting of hydrochloric acid, benzene sulfonic acid, or p-toluene sulfonic acid, formic acid or trifluoroacetic acid. However other mineral or organic acids can also be used.

It is preferred to use basic hydrolysis to eliminate acyl groups such as trifluoroacetyl such as a mineral base like sodium or potassium hydroxide but also useful are magnesia, baryta, or a carbonate or bicarbonate of an alkali metal such as the carbonates and bicarbonates of sodium or potassium or other bases. There can also be used sodium or potassium acetate. Hydrolysis using hydrazine is preferably used to eliminate groups such as phthaloyl.

When $R_b$ is trichloroethyl, it can also be eliminated by the zinc-acetic acid system. Benzhydryl and benzyloxycarbonyl groups are preferably removed with hydrogen in the presence of a catalyst. Chloroacetyl is eliminated by the action of thiourea in a neutral or acid medium by the reaction described by MASAKI J.A.C.S., 90, 4508, (1968). Other methods known in the literature for removing protective groups such as removal by oxidization particularly for benzyl are useful.

Among the preferred groups are formyl, acetyl, ethoxycarbonyl, mesyl, trifluoroacetyl, chloroacetyl and trityl, with trityl and chloroacetyl being particularly preferred. The preferred acid is trifluoroacetic acid or formic acid.

The elimination of the $R_b'$ radical or the protective groups which $R_b'$ and $R_a$ contain, when this is necessary, is carried out in similar conditions to those previously described for the elimination of $R_b$.

Acid hydrolysis, among others can be used to remove optionally substituted alkyl or aralkyl radicals. It is preferred to use an acid chosen from the group formed by hydrochloric acid, formic acid, trifluoroacetic acid and p-toluene sulfonic acid.

Other values for the $R_b$ or $R_b'$ or the protective groups which $R_b'$ or $R_a$ contain are removed, when this is desired, by processes known to the expert. It is preferred to operate under moderate conditions, such as at ambient temperature or with slight heating. Naturally, when, for example, $R_b$ or $R_b'$ or $R_a$ are or contain different groups which can be removed, several agents included in the previous lists can be made to act on the compounds of formula IV.

Salification of the products can be carried out by the usual methods. Salification can be effected by reacting a compound of formula I in the acid form or as a solvate such as the ethanol solvate or a hydrate of the acid with a mineral base such as sodium or potassium hydroxide or sodium or potassium carbonate or bicarbonate. There can also be utilized the salts of mineral acids such as tri-sodium phosphate as well as salts of organic acids. A list of such salts of organic acids can be found for example, in the French patent No. 2,476,087. It is preferred to use sodium acetate, sodium 2-ethyl hexanoate or sodium diethyl acetate. Salification can also be obtained by reaction with an organic base or of an amino acid.

The esterification, if required of the compounds of formula I wherein R is an acid function may also be carried out in standard conditions.

The sulfonation of the compounds of formula IV wherein A is hydrogen is carried out with sulfuric anhydride or a reactive derivative of the said anhydride.

It is preferred to use the complex of pyridine-sulfuric anhydride but also useful are other complexes of sulfuric anhydride with dioxane or trimethylamine. The reaction is carried out in usual solvents such as ethyl acetate, chloroform or dimethylformamide, and it can be effected at ambient temperature. When the complex pyridine-sulfuric anhydride is used, the products can be isolated in the form of pyridinium salts.

The resolution of the racemic molecules of formulae II or IV if desired can be carried out according to the usual methods. An optically active organic carboxylic acid or sulfonic acid such as tartaric acid, dibenzoyltartaric acid, camphosulfonic acid or glutamic acid can be used with the decomposition of the salt obtained being carried out with a mineral base such as sodium bicarbonate or an organic base such as a tertiary amine like triethylamine.

The invention is especially concerned with the process as described above wherein the compound of formula II wherein A is hydrogen is reacted with a compound of formula III wherein $R_b$ is a protective group for the amino, and the sulfonation is carried out with a compound of formula IV in which $R_b$ is a protective group for the amine.

The preferred protective group of $R_b$ is trityl. It is preferred to carried out the sulfonation with the complex pyridine sulfuric anhydride.

Also an object of the invention is a process for the preparation of the compounds of formula II by reacting a compound of the formula

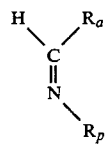   V wherein $R_a$ has the above definition and $R_p$ is a protective group for an imino with a compound of the formula

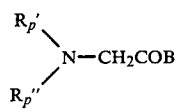   VI wherein one of $R_p'$ and $R_p''$ is hydrogen and the other is a protective group for an amino, or $R_p'$ and $R_p''$ together form a divalent protective group and B is hydroxyl or halogen to obtain a compound of the formula

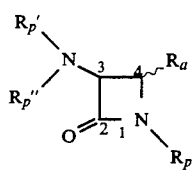   VII wherein $R_a$, $R_p$, $R_p'$ and $R_p''$ have the above definitions and the said product may be subjected to the following reactions:

a) Removal of $R_p$ by hydrolysis, hydrogenolysis or action of thiourea;

b) Possible sulfonation of the amine in the 1-position;

c) Removal of $R_p'$ and $R_p''$ by hydrolysis, hydrogenolysis or action of thiourea; and d) Possible resolution of the molecule to obtain an optically active product.

The protective group of $R_p$ can be selected from the list of substituents given above for amines. However, it is preferred to use a benzyl or 2,4-dimethoxy-benzyl or an equivalent.

In addition, the protective group $R_p$ can contain an asymmetric carbon atom and also an object of the invention is in particular a process as previously defined, characterised in that at the start a compound of formula (V) wherein $R_p$ represents a protective group of the imino radical containing an asymmetric group is used and a compound of formula (VII) is isolated in the optically active form.

These optically active products of formula (VII) lead to optically active compounds of formula (I) according to the process previously described.

As protective group, there can be cited particularly the 1-phenyl ethyl group.

An example of the preparation of an optically active compound of formula (VII) is provided further on in the experimental part.

Also $R_p'$ and $R_p''$ can be selected from the same list of protective radicals given above but it is preferred to use phthaloyl.

B can be halogen and the acid chloride is preferred. When B is halogen, the reaction of the compound of formula V with the compound of formula VI is carried out in the presence of a base such as triethylamine or of a metal such as zinc. When B is hydroxyl, the reaction is effected in the presence of a dehydratation agent such as an acid anhydride, preferably trifluoroacetic anhydride.

The action of the compounds of formula V with the compounds of formula VI gives cis products preferentially. Trans products are obtained by isomerization in a basic medium.

When it is required to sulfonate the compounds, the object of the first de-protection reaction is the selective deblocking of $R_p$. Therefore, as indicated above, it is preferred to utilize benzyl or di-methoxybenzyl which is preferably deblocked by an oxidizing agent such as potassium peroxodisulfate. It is preferred to operate in a solvent such as a water-acetic acid mixture or acetonitrile.

The sulfonation of compounds wherein the secondary amine in the 1-position is free is carried out as indicated above. The possible second deblocking operation is to liberate the amine in the 3-position by removal of the $R_p'$ and $R_p''$. When, as indicated above, phthalimido is used, the removal is effected with hydrazine, preferably hydrazine hydrate in a solvent such as dimethylformamide.

Naturally, in particular in the case where the sulfonation of the products of formula IV is not carried out, $R_p$, $R_p'$ and $R_p''$ can be eliminated simultaneously. Resolution, as indicated above, is carried out in the usual manner.

Also an object of the invention is a process for the preparation of compounds of the formula

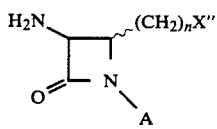   II$_a$ wherein A has the above definition, n is a whole number between 1 and 4 and X" is X, X having the significance indicated above with the exception of halogen, or X" is X in which a reactive function is protected comprising reacting a compound of the formula

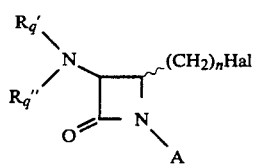   VIII wherein $R_q'$ and $R_q''$ each are hydrogen or have the significance of $R_p'$ and $R_p''$ indicated above, with a reactive derivative of cyano radical, of —OR$_1'$, —SR$_1''$,

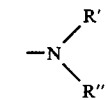

—SCN or —NCS to obtain a compound of the formula

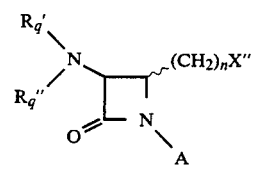   IX wherein X", A, $R_q'$ and $R_q''$ have the values indicated above, which product is optionally submitted to any one or more of the following reactions:

a) Removal of $R_q'$ and $R_q''$ when they are other than hydrogen by hydrolysis, hydrogenolysis or by action of thiourea;

b) Sulfonation of the products in which A is hydrogen;

c) Resolution of the molecule to obtain an optically active product.

The reaction of a compound of formula VIII with the reactive derivatives of the radicals which it is wished to substitute for the halogen atom is carried out under the usual conditions. For example, the exchange between a halogen and a mercaptan is preferably effected with an alkali metal salt of the mercaptan such as a sodium salt.

The exchange between the halogen atom and an alkali metal acetate such as sodium or potassium acetate enables a protected hydroxyl radical to be introduced which can be liberated and then, if desired, etherified. The action of an amine optionally protected by one of the radicals indicated above enables an optionally protected

to be introduced.

An alkali metal azide, preferably sodium azide, can be reacted to introduce the azido radical. An alkali metal cyanide or thiocyanate can also be reacted to obtain the products in which X is the said radicals or an isothiocyanate. The subsequent operations of possible de-protection, of sulfonation and of resolution, also possible, are carried out in the manner indicated above.

The novel antibiotic compositions of the invention are comprised of an antibiotically effective amount of at least one compound of formula I and their pharmaceutically acceptable salts and an inert pharmaceutical carrier or excipient. The compositions may be in the form of tablets, dragees, capsules, granules, suppositories, injectable solutions or suspensions, ointments, creams and gels prepared in the usual manner.

Examples of suitable excipients are talc, arabic gum, lactose, starch, magnesium stearate, cocoa butter, aqueous and non-aqueous vehicles, fatty bodies of animal or vegetable origin, paraffinic derivatives, glycols, various wetting, dispersing and emulsifying agents and preservatives. Especially useful are powders to be dissolved in an appropriate vehicle such as sterile apyrogeneous water.

The compositions of the invention have a very good antibiotic activity against Gram negative bacteria, particularly coliform bacteria, klebsiella, salmonella and proteus. The compositions can particularly be used as medicaments in the treatment of colibacilloses and associated infections, in proteus, klebsiella and salmonella infections and in other disorders caused by Gram negative bacteria.

Especially preferred are the compositions containing as the active ingredient a syn isomer of a cis compound of the formula

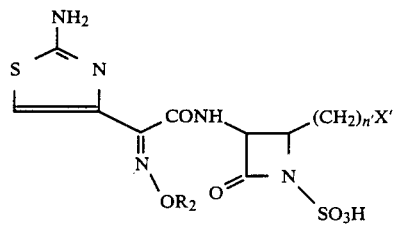

wherein $R_2$ is hydrogen or linear or branched alkyl optionally substituted with at least one halogen, —CN, carboxyl or amino, n' is 1 or 2 and X' is fluoro, thiocyanato or 2-pyridinylthiomethyl in racemic or optically active isomeric form and their salts with non-toxic, pharmaceutically acceptable acids or bases.

Especially preferred compositions of the invention are those of formula I' wherein n' is 1 and X is fluoro, those wherein $R_2$ is hydrogen, methyl, difluoromethyl, carboxymethyl optionally salified or esterified, aminoethyl, cyanomethyl or 1-methyl-1-carboxymethyl optionally salified or esterified and their non-toxic, pharmaceutically acceptable salts with acids and bases. The most preferred compositions are those containing the racemate or optically active isomer of the syn isomer of cis 4-fluoromethyl-3-[2(2-amino-4-thiazolyl)-2-methoxyimino-acetamido]-2-oxo-azetidine-1-sulfonic acid those containing the racemate or optically active isomer of the syn isomer of cis 4-fluoromethyl-3-[2(2-amino-4-thiazolyl)2-difluoromethoxyimino-acetamido]-2-oxo-azetidine-1-sulfonic acid and their pharmaceutically acceptable salts.

The novel method of the invention for combatting bacterial infections in warm-blooded animals, including humans, comprises administering to warm-blooded animals an antibacterically effective amount of at least one compound of formula I and their non-toxic, pharmaceutically acceptable salts of acids and bases. The compounds may be administered orally, rectally, parenterally or topically on the skin or mucous. The compositions may be administered at a dose of 3,5 to 50 mg/kg depending on the compound and the condition treated and the method of administration. For example, the compound of Example 1 may be orally administered at 0.250 to 4 g per day or intramuscularly at 0.500 to 1 g three times a day to humans. The compositions may also be used as disinfectants for surgical instruments.

The novel intermediates which are an object of the invention have the formulae

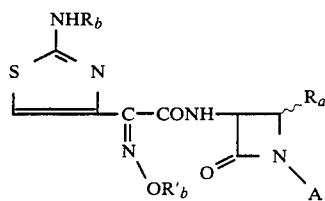

wherein $R_b$, $R_b'$, A and $R_a$ have the above definitions and

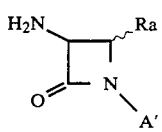

wherein $R_a$ has the above definition, and A' represents A whit the proviso that when A' is hydrogen, $R_a$ is not methylthio, hydroxymethyl, azidomethyl, amino methyl or alkoxymethyl and the wavy line indicates the cis form, trans form or cis trans form.

The starting compounds of formula V which are not known may be prepared by reacting an aldehyde of the formula $R_aCHO$ possibly in its hydrate form $R_aCH(OH)_2$ with a protected amine of the formula $R_pNH_2$.

Besides the compounds set forth in the specific working examples, other suitable compounds of formula I are illustrated in the following Table.

| R | $R_1$ |
| --- | --- |
| —$CH_2CH_3$ | —$CH_2Cl$ |
| —$(CH_2)_2CH_3$ | —$CH_2Cl$ |
| —$CH(CH_3)_2$ | —$CH_2Cl$ |
| -$nC_4H_9$ | —$CH_2Cl$ |
| —$CH_2$—CH=$CH_2$ | —$CH_2Cl$ |
| —$CH_2CO_2H$ | —$CH_2Cl$ |
| —C—$CO_2H$  | —$CH_2Cl$ |
| —$C(CH_3)_2CO_2H$ | —$CH_2Cl$ |
| —CH—$CO_2H$ \| $CH_3$ | —$CH_2Cl$ |
| —$CH_2CO_2C_2H_5$ | —$CH_2Cl$ |
| —$CH_2CO_2tBu$ | —$CH_2Cl$ |
| —CH—$CO_2H$ \| $C_2H_5$ | —$CH_2Cl$ |
| —$C(CH_3)_3$ | —$CH_2Cl$ |
| —$CH_2$—CH=CH—$CO_2H$ | —$CH_2Cl$ |
| —CH—$CO_2H$ \| $C_3H_7$ | —$CH_2Cl$ |
| —$CH_2CN$ | —$CH_2Cl$ |
| —$(CH_2)_2CN$ | —$CH_2Cl$ |
| —$CH_2$—$CONH_2$ | —$CH_2Cl$ |
| —$(CH_2)_2Br$ | —$CH_2Cl$ |
| —$(CH_2)_2Cl$ | —$CH_2Cl$ |
| —$(CH_2)_3Br$ | —$CH_2Cl$ |

-continued

| R | R₁ |
|---|---|
| —(CH₂)₂I | —CH₂Cl |
| —H₂C—C≡CH | —CH₂Cl |
| —HC=CH₂ | —CH₂Cl |
| —(CH₂)₂—N⁺(C₅H₅) (pyridinium) | —CH₂Cl |
| —(CH₂)₂—N(piperazine)NCH₃ | —CH₂Cl |
| —(CH₂)₂—N(morpholine)O | —CH₂Cl |
| —CH₂C(=O)—N(CH₃)₂ | —CH₂Cl |
| —CH₂—CH₂—N(CH₃)₂ | —CH₂Cl |
| H | —CH₂OCH₃ |
| CH₃ | —CH₂OCH₃ |
| —CH₂CH₂NH₂ | —CH₂OCH₃ |
| —CH₂CO₂H | —CH₂OCH₃ |
| —C(CH₃)₂CO₂H | —CH₂OCH₃ |
| —CH₂CH₂Br | —CH₂OCH₃ |
| —CH₂CH₂I | —CH₂OCH₃ |
| —CH₂CO₂C₂H₅ | —CH₂OCH₃ |
| —CH₂CO₂tBu | —CH₂OCH₃ |
| —C(CH₃)₂CO₂C₂H₅ | —CH₂OCH₃ |
| —C(CH₃)₂CO₂tBu | —CH₂OCH₃ |
| —CH₂CH₃ | —CH₂Br |
| —(CH₂)₂CH₃ | —CH₂Br |
| —CH(CH₃)₂ | —CH₂Br |
| -nC₄H₉ | —CH₂Br |
| —CH₂—CH=CH₂ | —CH₂Br |
| —CH₂CO₂H | —CH₂Br |
| —C—CO₂H (cyclopropyl) | —CH₂Br |
| —C(CH₃)₂CO₂H | —CH₂Br |
| —CH(CH₃)—CO₂H | —CH₂Br |
| —CH₂CO₂C₂H₅ | —CH₂Br |
| —CH₂CO₂tBu | —CH₂Br |
| —CH(C₂H₅)—CO₂H | —CH₂Br |
| —C(CH₃)₃ | —CH₂Br |
| —CH₂—CH=CH—CO₂H | —CH₂Br |
| —CH(C₃H₇)—CO₂H | —CH₂Br |
| —CH₂CN | —CH₂Br |
| —(CH₂)₂CN | —CH₂Br |
| —CH₂—CONH₂ | —CH₂Br |
| —(CH₂)₂Br | —CH₂Br |
| —(CH₂)₂Cl | —CH₂Br |
| —(CH₂)₃Br | —CH₂Br |
| —(CH₂)₂I | —CH₂Br |
| —H₂C—C≡CH | —CH₂Br |
| —HC=CH₂ | —CH₂Br |
| —(CH₂)₂—N⁺(C₅H₅) (pyridinium) | —CH₂Br |
| —(CH₂)₂—N(piperazine)NCH₃ | —CH₂Br |
| —(CH₂)₂—N(morpholine)O | —CH₂Br |
| —CH₂C(=O)—N(CH₃)₂ | —CH₂Br |
| —CH₂—CH₂—N(CH₃)₂ | —CH₂Br |
| CH₃ | —CH₂Br |
| —CH₂CH₂NH₂ | —CH₂Br |
| H | —CH₂Br |
| H | —CH₂SCH₃ |
| CH₃ | —CH₂SCH₃ |
| —CH₂CH₂NH₂ | —CH₂SCH₃ |
| —CH₂CO₂H | —CH₂SCH₃ |
| —C(CH₃)₂CO₂H | —CH₂SCH₃ |
| —CH₂CH₂Br | —CH₂SCH₃ |
| —CH₂CH₂I | —CH₂SCH₃ |
| —CH₂CO₂C₂H₅ | —CH₂SCH₃ |
| —CH₂CO₂tBu | —CH₂SCH₃ |
| —C(CH₃)₂CO₂C₂H₅ | —CH₂SCH₃ |
| —C(CH₃)₂CO₂tBu | —CH₂SCH₃ |
| —CH₂CH₃ | —CH₂OH |
| —(CH₂)₂CH₃ | —CH₂OH |
| —CH(CH₃)₂ | —CH₂OH |
| -nC₄H₉ | —CH₂OH |
| —CH₂—CH=CH₂ | —CH₂OH |
| —CH₂CO₂H | —CH₂OH |
| —C—CO₂H (cyclopropyl) | —CH₂OH |
| —(CH₃)₂CO₂H | —CH₂OH |
| —CH(CH₃)—CO₂H | —CH₂OH |
| —CH₂CO₂C₂H₅ | —CH₂OH |
| —CH₂CO₂tBu | —CH₂OH |
| —CH(C₂H₅)—CO₂H | —CH₂OH |
| —C(CH₃)₃ | —CH₂OH |
| —CH₂—CH=CH—CO₂H | —CH₂OH |
| —CH(C₃H₇)—CO₂H | —CH₂OH |
| —CH₂CN | —CH₂OH |
| —(CH₂)₂CN | —CH₂OH |
| —CH₂—CONH₂ | —CH₂OH |
| —(CH₂)₂Br | —CH₂OH |
| —(CH₂)₂Cl | —CH₂OH |
| —(CH₂)₃Br | —CH₂OH |
| H | —CH₂SCN |
| CH₃ | —CH₂SCN |
| —CH₂CH₂NH₂ | —CH₂SCN |
| —CH₂CO₂H | —CH₂SCN |
| —C(CH₃)₂CO₂H | —CH₂SCN |
| —(CH₂)₂I | —CH₂OH |

-continued

| R | R₁ |
|---|---|
| $-H_2C-C\equiv CH$ | $-CH_2OH$ |
| $-HC=CH_2$ | $-CH_2OH$ |
|  | $-CH_2OH$ |
| 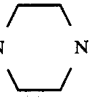 | $-CH_2OH$ |
| 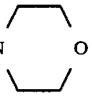 | $-CH_2OH$ |
| $-CH_2\overset{\text{O}}{\underset{\|}{C}}-N(CH_3)_2$ | $-CH_2OH$ |
| $-CH_2-CH_2-N(CH_3)_2$ | $-CH_2OH$ |
| $CH_3$ | $-CH_2OH$ |
| $-CH_2CH_2-NH_2$ | $-CH_2OH$ |
| H | $-CH_2OH$ |
| H | $CH_2NH_2$ |
| $CH_3$ | $CH_2NH_2$ |
| $-CH_2CH_2NH_2$ | $CH_2NH_2$ |
| $-CH_2CO_2H$ | $CH_2NH_2$ |
| $-C(CH_3)_2CO_2H$ | $CH_2NH_2$ |
| $-CH_2CH_2Br$ | $CH_2NH_2$ |
| $-CH_2CH_2I$ | $CH_2NH_2$ |
| H | $CH_2N_3$ |
| $CH_3$ | $CH_2N_3$ |
| $-CH_2CH_2NH_2$ | $CH_2N_3$ |
| $-CH_2CO_2H$ | $CH_2N_3$ |
| $-C(CH_3)_2CO_2H$ | $CH_2N_3$ |
| H | $CH_2NCS$ |
| $CH_3$ | $CH_2NCS$ |
| $-CH_2CH_2NH_2$ | $CH_2NCS$ |
| $-CH_2CO_2H$ | $CH_2NCS$ |
| $-CH_2CH_3$ | $CH_2SH$ |
| $-(CH_2)_2CH_3$ | $CH_2SH$ |
| $-CH(CH_3)_2$ | $CH_2SH$ |
| $-nC_4H_9$ | $CH_2SH$ |
| $-CH_2-CH=CH_2$ | $-CH_2SH$ |
| $-CH_2CO_2H$ | $-CH_2SH$ |
|  | $-CH_2SH$ |
| $-(CH_3)_2CO_2H$ | $-CH_2SH$ |
| $-\underset{\underset{CH_3}{\|}}{CH}-CO_2H$ | $-CH_2SH$ |
| $-CH_2CO_2C_2H_5$ | $-CH_2SH$ |
| $-CH_2CO_2tBu$ | $-CH_2SH$ |
| $-\underset{\underset{C_2H_5}{\|}}{CH}-CO_2H$ | $-CH_2SH$ |
| $-C(CH_3)_3$ | $-CH_2SH$ |
| $-CH_2-CH=CH-CO_2H$ | $-CH_2SH$ |
| $-\underset{\underset{C_3H_7}{\|}}{CH}-CO_2H$ | $-CH_2SH$ |
| $-CH_2CN$ | $-CH_2SH$ |
| $-(CH_2)_2CN$ | $-CH_2SH$ |
| $-CH_2-CONH_2$ | $-CH_2SH$ |
| $-(CH_2)_2Br$ | $-CH_2SH$ |
| $-(CH_2)_2Cl$ | $-CH_2SH$ |
| $-(CH_2)_3Br$ | $-CH_2SH$ |
| $-C(CH_3)_2CO_2H$ | $-CH_2NCS$ |
| H | $-CH_2N(CH_3)_2$ |
| $CH_3$ | $-CH_2N(CH_3)_2$ |
| $-CH_2CH_2NH_2$ | $-CH_2N(CH_3)_2$ |
| $-CH_2CO_2H$ | $-CH_2N(CH_3)_2$ |
| $-(CH_2)_2I$ | $-CH_2SH$ |
| $-H_2C-C\equiv CH$ | $-CH_2SH$ |
| $-HC=CH_2$ | $-CH_2SH$ |
| 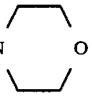 | $-CH_2SH$ |
| 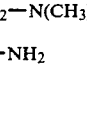 | $-CH_2SH$ |
| 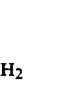 | $-CH_2SH$ |
| $-CH_2\overset{\text{O}}{\underset{\|}{C}}-N(CH_3)_2$ | $-CH_2SH$ |
| $-CH_2-CH_2-N(CH_3)_2$ | $-CH_2SH$ |
| $CH_3$ | $-CH_2SH$ |
| $-CH_2CH_2NH_2$ | $-CH_2SH$ |
| H | $-CH_2SH$ |
| $-C(CH_3)_2CO_2H$ | $-CH_2N(CH_3)_2$ |
| $-CH_2CN$ | $-CH_2F$ |
| $-CH_2-CO_2H$ | $-CH_2F$ |
| $-CH_3$ | 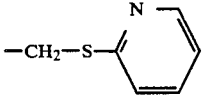 |
| $-CHF_2$ | 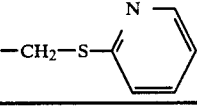 |

In the following examples there are described several preferred embodiments to illustrate the invention. However, it is to be understood that the invention is not intended to be limited to the specific embodiments.

EXAMPLE 1

Racemate of syn isomer of cis 4-chloromethyl-3-[2-(2-amino-4-thiazolyl)-2-methoxyimino-acetamido]-2-oxoazetidine-1-sulfonic acid Step A: 2-chloro-N-benzyl-ethanimine A solution of 4 ml of chloroacetaldehyde in 20 ml of demineralized water was cooled and a solution of 2.14 g of benzylamine in 10 ml of water was added thereto with stirring. After stirring for 5 minutes at 10° to 15° C., a gum was obtained and a turbid solution which was extracted with 30 ml and then with 20 ml of benzene. The organic solution was dried, filtered, rinsed and the filtrate was evaporated to dryness under vacuum to obtain 3.34 g of 2-chloro-N-benzylethanimine which was used as is for the next step.

Step B: Cis N-benzyl-3-phthalimido-4-chloromethyl-2-azetidinone

A solution of 3.34 g of the product of Step A in 20 ml of methylene chloride was cooled to −50° C. and 2.8 ml of triethylamine were added all at once. A solution of 4 g of phthalimidoacetic acid chloride in 20 ml of methylene chloride was added thereto over 20 minutes. The mixture was stirred for one hour at 0° to −5° C. and was then poured into a decanting flask. The decanted organic phase was washed with 50 ml of demineralized water and 5 ml of a molar aqueous solution of sodium bicarbonate, and then twice with 30 ml of demineralized water. The wash water was re-extracted with 20 ml of methylene chloride and the combined organic phases were dried, rinsed and evaporated to dryness under vacuum. The 6 g of residue were chromatographed over silica gel and eluted with methylene chloride containing 5% ether. The fraction with an Rf=0.45 was evaporated to dryness and the residue was triturated with 10 ml of ether. The separated product was rinsed three times with 2 ml of ether and dried under vacuum to obtain 1.25 g of cis N-benzyl-3-phthalimido-4-chloromethyl-2-azetidinone melting at 149° C.

Step C: Cis 3-phthalimido-4-chloromethyl-2-azetidinone

A mixture of 17.75 g of the product of Step B, 31 g of potassium peroxodisulfate, 110 ml of water and 160 ml of acetic acid was heated for 25 minutes with strong agitation in an oil bath at 120° C. and was then cooled to room temperature. 50 g of dipotassium phosphate were added to the mixture to adjust the pH to neutrality and was evaporated to dryness under reduced pressure. 250 ml of water and 150 ml of ethyl acetate were added to the residue and after stirring, sodium bicarbonate was added in small quantities until evolution of gas ceased. The mixture was filtered and the filtrate was rinsed with ethyl acetate. The decanted aqueous phase was re-extracted with 50 ml of ethyl acetate and the combined organic phases were dried, filtered, rinsed and evaporated to dryness under reduced pressure. The residue was chromatographed over 200 g of silica gel and eluted with methylene chloride with 25% of ethyl acetate. The rich fractions were recovered and evaporated to dryness. The residue was dissolved in ether, and the solution was rinsed and dried to obtain 5.4 g of cis 3-phthalimido-4-chloromethyl-2-azetidinone.

| Analysis: $C_{12}H_9N_2Cl$; molecular weight = 264.67 | | |
|---|---|---|
| | % C | % H |
| Calculated: | 54.46 | 3.43 |
| Found: | 54.7 | 3.5 |

Step D: 4-chloromethyl-3-amino-2-oxo-azetidine hydrochloride 12 ml of a solution of 2 ml of hydrazine hydrate in 20 ml of dimethylformamide was added dropwise to a solution of 5.3 g of the product of Step C in 5.4 ml of methylene chloride. After stirring, the mixture stood for 20 minutes and about 30 ml of hydrochloric acid were added thereto to form a complete solution with a pH of 3. After stirring for 18 hours at room temperature, the mixture was filtered. The filter was rinsed with water, then with ethanol and finally with ether and evaporated to dryness to obtain 2.844 g of product. The filtrate was evaporated to dryness under reduced pressure and the residue was taken up twice with ethanol. The ethanol phase was evaporated to dryness and the residue was added to 20 ml of ethanol. The mixture was stirred for 45 minutes and vacuum filtered. The crystals were rinsed with ethanol and ether to obtain 2.466 g of 4-chloromethyl-3-amino-2-oxo-azetidine hydrochloride.

Step E: Syn isomer of 4-chloromethyl-3-[2-(2-tritylamino-4-thiazolyl)-2-methoxyimino-acetamido]-2-oxo-azetidine A suspension of 2.32 g of the syn isomer of 2-(2-tritylamino-4-thiazolyl)-2-methoxyimino-acetamido acid in 23 ml of methylene chloride was cooled and 594 mg of dicyclohexylcarbodiimide were added thereto. The mixture was stirred cold for 20 minutes while adding thereto a solution of 441 mg of 4-chloromethyl-3-amino-2-oxo-azetidine hydrochloride in 10 ml of methylene chloride and 0.4 ml of triethylamine. After stirring for 80 minutes at room temperature, the dicyclohexylurea formed was separated by filtration. The filtrate was rinsed with methylene chloride, and 10 ml of a saturated solution of sodium bicarbonate and 20 ml of water were added to the filtrate which was then stirred. The decanted organic phase was washed with water and the organic phase was re-extracted and dried and evaporated to dryness under reduced pressure. A minimum of ethyl acetate was added to the residue and the mixture was filtered. The filter was rinsed with ethyl acetate and the filtrate was evaporated to dryness under reduced pressure. The residue was dissolved in 5 ml of ethanol and the solution was slowly diluted with 10 ml of ether. Crystallization was initiated and the mixture was stirred for 2 hours and vacuum filtered. The product was rinsed with an 1-2-ethanol-ether mixture to obtain 688 mg of syn isomer of 4-chloromethyl-3-[2-(2-tritylamino-4-thiazolyl)-2-methoxyimino-acetamido]-2-oxo-azetidine.

| Analysis: $C_{29}H_{26}O_3N_5SCl$; molecular weight = 560.08 | | | |
|---|---|---|---|
| | % C | % H | % N |
| Calculated: | 62.19 | 4.68 | 12.5 |
| Found: | 62.4 | 4.8 | 12.2 |

Step F: Racemate of syn isomer of cis 4-chloromethyl-3-[2-(2-amino-4-thiazolyl)-2-methoxyimino-acetamido]-2-oxo-azetidine-1-sulfonic acid 2.403 g of the product of Step E were added to a solution of 1.72 g of pyridine sulfan (complex of sulfuric acid-pyridine anhydride) in 17.2 ml of dry dimethylformamide and after stirring the mixture for 66 hours at room temperature, the mixture was filtered. The filter was rinsed with dimethylformamide and the filtrate was diluted with 300 ml of ether. The mixture was stirred and allowed to stand for 10 minutes. The mixture was evaporated to dryness and the residue was triturated with ether. The gum was taken up in 20 ml of ethanol and after dissolving and scratching, the expected product crystallized out. The mixture was lightly stirred for 30 minutes and was filtered. The product was rinsed with ethanol and then with ether to obtain 855 mg of cis pyridinium 4-chloromethyl-3-[2-(2-tritylamino-4-thiazolyl)-2-methoxyimino-acetamido]-2-oxo-azetidine-1-sulfonate.

A mixture of 360 mg of the said product and 1.4 ml of formic acid with 33% water was heated to 50° C. to effect dissolution and crystallization of triphenylcarbinol occured. The mixture was left for 10 minutes at 50° C., cooled, diluted with 0.6 ml of water and was filtered. The filter was rinsed with water and a little ethanol was added to the filtrate, which was evaporated to dryness under reduced pressure. Water and ethanol were added to the residue and the mixture was evaporated under vacuum to dryness. 1.2 ml of a saturated aqueous solution of sodium bicarbonate were added to the residue and the mixture was filtered. The filter was rinsed with water and 3 drops of formic acid were added to the filtrate. Crystallization was induced and the mixture was stirred for 10 minutes and filtered. The product was rinsed with water and with ether and dried to obtain 113 mg of racemate of syn isomer of cis 4-chloromethyl-3-[2-(2-amino-4-thiazolyl)-2-methoxyimino-acetamido]-2-oxo-azetidine-1-sulfonic acid.

| Analysis: $C_{10}H_{12}O_6N_5S_2Cl$ - molecular weight = 397.82 | | |
|---|---|---|
| | % C | % H |
| Calculated: | 30.19 | 3.04 |
| Found: | 29.6 | 3.2 |

EXAMPLE 2

Racemate of syn isomer of cis 4-(1-methyl-5-mercapto-1,2,3,4-tetrazol)-methyl-3-[2-(2-amino-4-thiazolyl)-2-methoxyiminoacetamido]-2-oxo-azetidine-1-sulfonic acid

Step A: Cis 4-(1-methyl-5-mercapto-1,2,3,4-tetrazol)-methyl-3-phthalimido-2-oxo-azetidine A suspension of 7.6 g of cis 4-chloromethyl-3-phthalimido-2-oxo-azetidine obtained by Step C of Example 1, 5.48 g of sodium salt of 1-methyl-5-mercapto 1,2,3,4-tetrazole (dihydrated), 4.3 g of sodiuym iodide and 57 ml of dimethylformamide was heated to 100° C. and stirred for 3 hours at this temperature and then cooled. The mixture was poured into 0.75 liters of water and 150 ml of ethyl acetate and was rinsed with water. The mixture was vigorously stirred and the decanted phase was re-extracted with 75 ml and then 45 ml of ethyl acetate, and was filtered. The filtrate was washed with 150 ml of water, dried and filtered. The filtrate was concentrated to a small volume under reduced pressure, filtered a second time and rinsed with ethyl acetate. The combined insoluble products were dried to obtain 5.1 g of cis 4-(1-methyl-5-mercapto-1,2,3,4-tetrazol)-methyl-3-phthalimido-2-oxo-azetidine.

| Analysis: $C_{14}H_{12}O_3N_6S$ ¼ AcOEt; molecular weight = 366.37 | | | |
|---|---|---|---|
| | % C | % H | % N |
| Calculated: | 49.17 | 3.85 | 22.94 |
| Found: | 49.2 | 3.7 | 23.0 |

Step B: Cis-4-(1-methyl-5-mercapto-1,2,3,4-tetrazol)-methyl-3-amino-2-oxo-azetidine hydrochloride 1 ml of hydrazine hydrate was added dropwise to a suspension of 5.845 g of the product of Step A in 18.5 ml of anhydrous dimethylformamide and the mixture was stirred for 20 minutes at room temperature. 19 ml of water and 24 ml of N hydrochloric acid were added to the mixture which had a pH of 3. The mixture stood overnight with stirring at room temperature and was then filtered. The filtrate was rinsed with water and evaporated to dryness under reduced pressure. After adding ethanol to the residue, the mixture was triturated and evaporated to dryness. The residue was dissolved in hot methanol which solution was evaporated to dryness. The residue was added to 20 ml of methanol, triturated, iced and filtered. The product was rinsed with iced methanol and with ether to obtain 2.49 g of cis 4-(1-methyl-5-mercapto-1,2,3,4-tetrazol)-methyl-3-amino-2-oxo-azetidine-hydrochloride.

Step C: Cis 4-(1-methyl-5-mercapto-1,2,3,4-tetrazol)-methyl-3-[2-(2-tritylamino-4-thiazolyl)-2-methoxyimino-acetamido]-2-oxo-azetidine-1-sulfonic acid A mixture of 2.25 g of the syn isomer of 2-(2-tritylamino-4-thiazolyl)-2-methoxyimino-acetic acid in 21 ml of methylene chloride and 576 mg of dicyclohexylcarbodiimide was stirred for 20 minutes in a bath of iced water and the bath was removed. A solution of 597 mg of 4-(1-methyl-5-mercapto-1,2,3,4-tetrazol)-methyl-3-amino-2-oxo-azetidine hydrochloride in 10 ml of methylene chloride and 0.38 ml of triethylamine was added thereto and the mixture was stirred at room temperature for 80 minutes and evaporated to dryness under reduced pressure. The residue was rinsed with methylene chloride, then with ether and dried to obtain 1.594 g of product containing dicyclohexylurea.

A mixture of 1.594 g of the said product and 0.66 g of pyridine sulfan (complex pyridine-sulfuric anhydride) in 6.6 ml of dimethylformamide was agitated for 70 hours. The dicyclohexylurea was filtered off. The filter was rinsed with a minimum of dimethylformamide and the filtrate was diluted with about 200 ml of ether. After stirring well, the mixture was filtered and washed with ether. The combined products were dissolved in methanol and crystallization occured. The mixture was filtered and the product was rinsed with methanol then with ether and dried to obtain 620 mg of cis-4-(1-methyl-5-mercapto-1,2,3,4-tetrazol)-methyl-3-[2-(2-tritylamino-4-thiazolyl)-2-methoxyimino-acetamido]-2-oxo-azetidine-1-sulfonic acid.

Step D: Racemate of syn isomer of cis 4-(1-methyl-5-mercapto-1,2,3,4-tetrazol)-methyl-3[2(2-amino-4-thiazolyl)-2-methoxyimino-acetamido]-2-oxo-azetidine-1-sulfonic acid.

A mixture of 620 mg of the product of Step C in 0.8 ml of water and 1.62 ml of formic acid was heated to 60° C. for 12 minutes and triphenylcarbinol crystallized out. By cooling and diluting the mixture with a little water, additional product crystallized. The mixture was agitated for 10 minutes and was filtered. The product was rinsed with water and triturated three times with ether. The insoluble product was dissolved in water and 2 ml of saturated aqueous sodium bicarbonate were added. The mixture was stirred and filtered. The filtrate was rinsed with water and N hydrochloric acid was added to ajust the pH to 2 and crystallization occured. After stirring for 5 minutes, the mixture was filtered and the product was rinsed with water and then with ether and dried to obtain 294 mg of racemate of syn isomer of cis 4-(1-methyl-5-mercapto-1,2,3,4-tetrazol)-methyl-3-[2-(2-amino-4-thiazolyl)-2-methoxyimino-acetamido]-2-oxo-azetidine-1-sulfonic acid.

| Analysis: $C_{12}H_{15}O_6N_9S_3 \cdot \frac{1}{2} H_2O$; molecular weight = 486.51 | | | | |
|---|---|---|---|---|
| | % C | % H | % N | % S |
| Calculated: | 29.63 | 3.31 | 25.91 | 19.77 |
| Found: | 29.5 | 3.4 | 25.8 | 19.8 |

EXAMPLE 3

Racemate of syn isomer of cis 4-chloromethyl-3[2-(2-amino-4-thiazolyl)-2-(2-aminoethoxy)-imino-acetamido]-2-oxo-azetidine-1-sulfonic acid

Step A: Syn isomer of 4-chloromethyl-3-[2(2-tritylamino-4-thiazolyl)-2-(2-tritylamino-ethoxy)-imino-acetamido]-2-oxo-azetidine A mixture of 1.68 g of tosyl chloride and a solution of 6.3 g of the syn isomer of 2-(2-tritylamino-4-thiazolyl)-2-(2-tritylamino-ethoxy)-imino-acetic acid in 40 ml of methylene chloride and 1.24 ml of triethylamine was stirred for 40 minutes and then a solution of 1.368 g of 4-chloromethyl-3-amino-2-oxo-azetidine hydrochloride in 40 ml of methylene chloride and 2.4 ml of triethylamine was added thereto all at once. The mixture was stirred for 2 hours at room temperature and water was added thereto with vigorous stirring. The aqueous phase was extracted with methylene chloride and the combined organic phases were dried, filtered and evaporated to dryness. The residue was chromatographed over silica gel and was eluted with ether to obtain 4.9 g of syn isomer of 4-chloromethyl-3-[2-(2-tritylamino-4-thiazolyl)-2-(2-tritylamino-ethoxy)-imino-acetamido]-2-oxo-azetidine with an Rf=0.8.

Step B: Pyridinium 4-chloromethyl-3-[2-(2-tritylamino-4-thiazolyl)-2-(2-tritylamino-ethoxy)-imino-acetamido]-2-oxo-azetidine-1-sulfonate A mixture of 4.9 g of the product of Step A, 2.6 g of pyridine sulfan and 25 ml of dimethylformamide was stirred at room temperature for 4 days and was then poured into one liter of water containing 500 ml of ether. The insolubles were triturated and filtered. The product was rinsed with ether and dried to obtain 6.6 g of pyridinium 4-chloromethyl-3-[2-(2-tritylamino-4-thiazolyl)-2-(2-tritylamino-ethoxy)-imino-acetamido]-2-oxo-azetidine-1-sulfonate with an Rf=0.4 (eluant -65-20-15 methylene chloride-ethyl acetate-ethanol mixture).

Step C: Racemate of syn isomer of cis 4-chloromethyl-3-[2-(2-amino-4-thiazolyl)-2-(2-aminoethoxy)-imino-acetamido]-2-oxo-azetidine-1-sulfonic acid A suspension of 5.3 g of the product of Step B in 42 ml of formic acid containing 33% water was heated at 55 to 60° C. for 12 minutes and was cooled and diluted with 30 ml of water. The mixture was filtered and the filter was rinsed with water. The filtrate was evaporated to dryness in a water bath at 40° C. The residue was twice taken up in a water-ethanol mixture and evaporated to dryness. The residue was added to water and the pH was made alkaline by slow addition of aqueous saturated sodium bicarbonate solution. The mixture was filtered and the filter was rinsed with water, 2N hydrochloric acid was added to the filtrate to adjust the pH to 4–5 and crystallization was effected. The mixture was stirred for one hour and was filtered. The product was rinsed with water and then with ether to obtain 700 mg of racemate of syn isomer of cis 4-chloromethyl-3-[2-(2-amino-4-thiazolyl)-2-(2-aminoethoxy)-imino-acetamido]-2-oxo-azetidine-1-sulfonic acid.

| Analysis: $C_{11}H_{15}O_6N_6S_2Cl$ | | |
|---|---|---|
| | % C | % H |
| Calculated: | 30.95 | 3.54 |
| Found: | 30.9 | 3.8 |

EXAMPLE 4

Racemate of syn isomer of cis 4-chloromethyl-3-[2-(2-amino-4-thiazolyl)-2-hydroxyimino-acetamido]-2-oxo-azetidine-1-sulfonic acid

Step A: Syn isomer of 4-chloromethyl-3-[2-tritylamino-4-thiazolyl)-2-trityloxyimino-acetamido]-2-oxo-azetidine A mixture of 1.527 g of the syn isomer of sodium 2-(2-tritylamino-4-thiazolyl)-2-trityloxyimino-acetic acid, 419 mg of tosyl chloride and 15 ml of methylene chloride was stirred for 40 minutes and then a solution of 342 mg of 4-chloromethyl-3-amino-2-oxo-azetidine hydrochloride in 15 ml of methylene chloride and 0.6 ml of triethylamine was added thereto. The mixture was stirred for 2 hours and water was added thereto with stirring. The decanted aqueous phase was extracted with methylene chloride and the combined organic phases were dried, filtered and evaporated to dryness under reduced pressure. The residue was chromatographed over silica gel and was eluted with ether to obtain 736 mg of syn isomer of 4-chloromethyl-3-[2-(2-tritylamino-4-thiazolyl)-2-trityloxyimino-acetamido]-2-oxo-azetidine.

Step B: Pyridinium 4-chloromethyl-3-[2-(2-tritylamino-4-thiazolyl)-2-trityloxyimino-acetamido]-2-oxo-azetidine-1-sulfonate A solution of 1.248 g of the product of Step A, 640 mg of pyridine sulfan and 6.8 ml of anhydrous dimethylformamide stood at room temperature for 4 hours and was then poured into 300 ml of ether. The mixture was triturated and filtered and the product was rinsed with ether and empasted with 10 ml of methanol. The mixture was stirred for 15 minutes and was filtered. The product was rinsed with methanol and with ether and dried to obtain 1.02 g of pyridinium 4-chloromethyl-3-[2-(2-tritylamino-4-thiazolyl)-2-trityloxyimino-acetamido]-2-oxo-azetidine-1-sulfonate.

Step C: Racemate of syn isomer of cis 4-chloromethyl-3-[2-(2-amino-4-thiazolyl)-2-hydroxyimino-acetamido]-2-oxo-azetidine-1-sulfonic acid A suspension of 1.02 g of the product of Step B in 9.1 ml of formic acid containing 33% water was heated at 60° C. for 15 minutes and was reacted as in Step C of Example 3 to obtain 119 mg of racemate of syn isomer of cis 4-chloromethyl-3-[2-(2-amino-4-thiazolyl)-2-hydroxyimino-acetamido]-2-oxo-azetidine-1sulfonic acid.

EXAMPLE 5

Racemate of syn isomer of cis 4-fluoromethyl-3-[2-(2-amino-4-thiazolyl)-2-methoxyimino-acetamido]-2-oxo-azetidine-1-sulfonic acid

Step A: N-methyl-N-methoxy-fluoroacetamide 50 ml of methoxymethylamine were slowly added under an inert atmosphere to a mixture of 27.2 g of fluoroacetyl fluoride in 120 ml of methylene chloride at 5° C. while keeping the temperature below 20° C. and the mixture was stirred at 20° C. for 2 hours and was then filtered. The mixture was evaporated to dryness and the residue was rectified under reduced pressure to obtain 30.9 g of N-methyl-N-methoxyfluoroacetamide boiling at 93° C. at 23 mm Hg.

Step B: Fluoroacetaldehyde hydrate 74 ml of a 1M solution of diisobutyl aluminum hydride in hexane were slowly added at 2° C. to a solution of 7.8 g of the product of Step A in 133 ml of tetrahydrofuran and the temperature was allowed to slowly rise to room temperature. The mixture was poured into a mixture of 28 ml of concentrated hydrochloric acid and 56 ml of water with cooling and the mixture was distilled at atmospheric pressure to obtain 38 ml of fluoroacetaldehyde hydrate diluted with water with a boiling point of 75° to 100.5° C.

Step C: Cis 4-fluoromethyl-3-phthalimido-2-oxo-1-(1-phenylethyl)-azetidine 8.8 ml of DL α-phenyl-ethylamine were added over 15 minutes to a mixture of 69 ml of the solution of Step B and 100 ml of water cooled in an ice bath and the mixture was stirred for 10 minutes and was filtered. The filter was rinsed with water and the filtrate was added to 130 ml of methylene chloride. The mixture was refluxed until total dissolution occured and was cooled. The decanted organic phase was dried and cooled to −50° C. under an inert atmosphere while slowly adding thereto a solution of 15.4 g of phthalimidoacetyl chloride, 60 ml of methylene chloride and 10.4 ml of triethylamine. The temperature was allowed to rise to 20° C. and stirred for one hour at 20° C. 25 ml of 10% sodium bicarbonate solution and 60 ml of water were added thereto with stirring and the mixture was extracted with methylene chloride. The organic phase was dried and evaporated to dryness under reduced pressure. The residue was chromatographed over silica gel and was eluted with methylene chloride containing 10% ether to obtain 13.7 g ofcis 4-fluoromethyl-3-phthalimido-2-oxo-1-(1-phenyl-ethyl)-azetidine.

Analysis: $C_{20}H_{17}O_3N_2F$; molecular weight = 352.37

|  | % C | % H | % N | % F |
|---|---|---|---|---|
| Calculated: | 68.17 | 4.86 | 7.95 | 5.39 |
| Found: | 68.2 | 4.9 | 7.8 | 5.6 |

Step D: Racemate of cis 4-fluoromethyl-3-phthalimido-2-oxo-azetidine 130 ml of water were added to a solution of 13.7 g of Step C in 200 ml of acetonitrile and a solution of 22.2 g of ammonium persulfate in 52 ml of water were added thereto at reflux. The mixture was refluxed for 105 minutes and was cooled. The mixture was saturated with sodium chloride and the decanted organic phase was washed with aqueous saturated sodium chloride solution. The wash water was extracted with ethyl acetate and the combined organic phases were dried and evaporated to dryness. The residue was chromatographed over silica gel and was eluted with a 3-1 methylene chloride-ethyl acetate mixture. The product was washed with ether to obtain 3.756 g of racemate of cis 4-fluoromethyl-3-phthalimido-2-oxo-azetidine.

IR Spectrum (chloroform): Absorption at 3430 cm$^{-1}$ (NH); at 1790, 1770 and 1725 cm$^{-1}$ (c=O of β-lactam and phthalimido).

Step E: Cis 4-fluoromethyl-3-amino-2-oxo-azetidine hydrochloride 14 ml of a solution of 1 ml of hydrazine hydrate in 50 ml of dioxane were added to a suspension of 1.24 g of the product of Step D in 1.2 ml of dioxane and the mixture was stirred at room temperature for 45 minutes and 5 ml of N hydrochloric acid were added thereto. The mixture was stirred for 15 hours and was evaporated to dryness. The residue was added to water and 2.3 ml of N hydrochloric acid with stirring and the mixture was filtered. Ethanol was added to the filtrate and the mixture was evaporated to dryness. Methanol was added to the residue followed by ethanol addition and the mixture was evaporated to dryness. The product was crystallized from methanol to obtain 0.391 g of cis 4-fluoromethyl-3-amino-2-oxo-azetidine hydrochloride melting at ≈220° C. (decomposition).

Step F: Racemate of syn isomer of cis 4-fluoromethyl-3-[2-(2-tritylamino-4-thiazolyl)-2-methoxyimino-acetamido]-2-oxo-azetidine A mixture of 0.915 g of the syn isomer of 2-(2-tritylamino-4-thiazolyl)-2-methoxyimino-acetic acid, 7 ml of acetone and 0.319 g of tosyl chloride was stirred at 20° C. for 50 minutes and was filtered and a solution of 0.216 g of the product of Step E, 0.42 ml of triethylamine and 7 ml of methylene chloride were added thereto. The mixture was stirred for 45 minutes and was evaporated to dryness. The residue was added to water with efflorescence and was vacuum filtered. The product was empasted with acetone and was vacuum filtered. The product was empasted with ethyl acetate to obtain 0.654 g of racemate of syn isomer of cis 4-fluoromethyl-3-[2-(2-tritylamino-4-thiazolyl)-2-methoxyimino-acetamido]-2-oxo-azetidine.

Analysis: $C_{29}H_{26}O_3N_5SF$; molecular weight = 543.62

|  | % C | % H | % N | % S | % F |
|---|---|---|---|---|---|
| Calculated: | 64.07 | 4.82 | 12.88 | 5.90 | 3.49 |
| Found: | 64.0 | 4.9 | 12.4 | 5.9 | 3.4 |

Step G: Racemate of syn isomer of cis 4-fluoromethyl-3-[2-(2-amino-4-thiazolyl)-2-methoxyimino-acetamido]-2-oxo-azetidine-1-sulfonic acid A mixture of 0.564 g of the product of Step F, 0.410 g of pyridine sulfan and 4.1 ml of dimethylformamide was stirred at 20° C. for 88 hours and was then poured into 200 ml of ether. The mixture was vacuum filtered and the product was stirred with methanol and vacuum filtered. The crystals were dried to obtain 0.473 of the pyridinium salt of the racemate of the syn isomer of cis 4-fluoromethyl-3-[2-(2-tritylamino-4-thiazolyl)-2- methoxyimino-acetamido]-2-oxo-azetidine-1-sulfonic acid.

A suspension of 0.470 g of the said product in 1.87 ml of formic acid containing 33% of water was heated at 55° to 60° C. for 5 minutes and then at 70° C. for 13 minutes and 1.2 ml of formic acid were added thereto. The mixture was heated at 70° C. for 15 minutes and was cooled to 20° C. and filtered. Ethanol was added to the filtrate which was then evaporated to dryness. The residue was added to water and ethanol and the mixture was evaporated to dryness. The residue was dissolved in water and 1.6 ml of 10% aqueous sodium bicarbonate solution was added thereto. The mixture was filtered and 2N hydrochloric acid was added to the filtrate to adjust the pH to 2. The water was evaporated and the residue was empasted with water. The mixture was filtered and the product was rinsed with water, then with ether and dried to obtain 0.140 g of racemate of syn isomer of cis 4-fluoromethyl-3-[2-(2-amino-4-thiazolyl)-2-methoxyimino-acetamido]-2-oxo-azetidine-1-sulfonic acid melting at ≃240° C. with decomposition.

| Analysis: $C_{10}H_{12}O_6N_5S_2F$; molecular weight = 381.36 | | | | | |
|---|---|---|---|---|---|
| | % C | % H | % N | % S | % F |
| Calculated: | 31.50 | 3.17 | 18.36 | 16.81 | 4.98 |
| Found: | 31.6 | 3.2 | 18.5 | 16.5 | 5.1 |

EXAMPLE 6

Racemate of syn isomer of cis 4-fluoromethyl-3-[2-(2-amino-4-thiazolyl)-2-(1-carboxy-1-methyl-ethoxy)-imino-acetamido]-2-oxo-azetidine-1-sulfonic acid Step A: Racemate of the syn isomer of cis 4-fluoromethyl-3-[2-(2-tritylamino-4-thiazolyl)-2-(1-tertbutoxycarbonyl-1-methyl-ethoxy)-imino-acetamido]-2-oxo-azetidine 0.229 g of tosyl chloride was added to a mixture of 0.686 g of the syn isomer of 2-(2-tritylamino-4-thiazolyl)-2-(1-tertbutoxycarbonyl-1-methyl-ethoxy)-imino-acetic acid (described in French patent Application No. 2,421,906), 5 ml of acetone and 0.17 ml of triethylamine and the mixture was stirred for 50 minutes and filtered. A solution of 0.155 g of cis 4-fluoromethyl-3-amino-2-oxo-azetidine hydrochloride in 5 ml of methylene chloride and 0.3 ml of triethylamine was added with stirring to the filtrate and the mixture was stirred for 55 minutes at 20° C. The mixture was evaporated to dryness and the residue was added to methylene chloride and water. 2 ml of 10% aqueous sodium bicarbonate solution were added to the stirred mixture and the decanted aqueous phase was extracted with methylene chloride. The combined organic phases were evaporated to dryness and the residue was chromatographed over silica gel. Elution with ether yielded 0.613 g of racemate of the syn isomer of cis 4-fluoromethyl-3-[2-(2-tritylamino-4-thiazolyl)-2-(1-tert butoxycarbonyl-1-methylethoxy)-imino-acetamido]-2-oxo-azetidine.

Step B: Racemate of the syn isomer of cis 4-fluoromethyl-3-[2-(2-amino-4-thiazolyl)-2-(1-carboxy-1-methyl-ethoxy)-iminoacetamido]-2-oxo-azetidine-1-sulfonic acid A solution of the product of Step A, 0.36 g of pyridine sulfan and 3.6 ml of dimethylformamide was stirred at 20° C. for 62 hours and was then poured into water. The stirred mixture was vacuum filtered and the product was dried to obtain 0.518 g of the pyridinium salt of the racemate of the syn isomer of cis 4-fluoromethyl-3-[2-(2-tritylamino-4-thiazolyl)-2-(1-carboxy-1-methyl-ethoxy)-imino-acetamido]-2-oxo-azetidine-1-sulfonic acid. A solution of the said product in 2.9 ml of trifluoroacetic acid was held at 20° C. for 15 minutes and 29 ml of isopropyl ether were added thereto. The mixture was filtered and the product was empasted with ethyl acetate for 15 minutes and was filtered. The product was dried and dissolved in a small amount of water containing 1 ml of 10% sodium bicarbonate solution. The mixture was filtered and the pH of the filtrate was adjusted to 2 by addition of 2N hycrochloric acid. The mixture was filtered and the water was partially evaporated. The mixture was iced and vacuum filtered. The crystals were rinsed with ether to obtain 0.094 g of racemate of the syn isomer of cis 4-fluoromethyl-3-[2-(2-amino-4-thiazolyl)-2-(1-carboxy-1-methyl-ethoxy)-iminoacetamido]-2-oxo-azetidine-1-sulfonic acid melting at ≃230° C. (decomposition).

NMR Spectrum (dimethylsulfoxide-90 MHz): Peaks at 1.5 ppm (hydrogens of methyl); 3.78 to 4.94 ppm (4-hydrogen and hydrogens of —CH$_2$F); at 5.22–5.27–5.32–5.37 ppm (4-hydrogen); at 6.88 ppm (5-hydrogen of syn thiazole); at 9.21 and 9.31 ppm (hydrogen of

EXAMPLE 7

Racemate of the syn isomer of cis 4-thiocyanatomethyl 3-[2-(2-amino 4-thiazolyl)-2-methoxyimino-acetamido]-2-oxo-azetidine-1-sulfonic acid Step A: Racemate of cis 4-iodomethyl-3-phthalimido-2-oxo-azetidine A mixture of 26.5 g of cis 4-chloromethyl-3-phthalimido-2-oxo-acetidine, 30 g of sodium iodide and 80 ml of dimethylformamide was heated at 120° C. for 2 hours and was cooled and poured into a mixture of 800 ml of water and 100 ml of ethyl acetate with stirring. The mixture was filtered and the product was rinsed with water, then with ethyl acetate until decoloration occured and with ether. The mother liquors were decanted and the organic phase was evaporated to dryness. The residue was taken up in ethyl acetate and the solution was filtered. The product was raised with ethyl acetate and dried to obtain 2 crops totalling 28.4 g of racemate of cis 4-iodomethyl-3-phthalimido-2-oxo-azetidine.

Step B: Racemate of cis 4-thiocyanatomethyl-3-phthalimido-2-oxo-azetidine 1.5 g of potassium thiocyanate were added at 75° C. with stirring to a mixture of 1.78 g of the product of Step A in 5 ml of dimethylformamide and the mixture was stirred for 3½ hours and was poured into water. The mixture was vacuum filtered and the product was washed with water and dried. The product was empasted with hot isopropyl ether, vacuum filtered and dried to obtain 1.25 g of racemate of cis 4-thiocyanatomethyl-3-phthalimido-2-oxo-azetidine.

Step C: Cis 4-thiocyanatomethyl-3-amino-2-oxo-azetidine hydrochloride

A hot mixture of 1.45 g of the product of Step B in 15 ml of hot dioxane was cooled and 0.3 ml of hydrazine hydrate was added thereto. The mixture was stirred for 50 minutes at 20° C. and 7.5 ml of N hydrochloric acid were added thereto. The mixture was stirred for 15 hours and vacuum filtered. The filtrate was rinsed with water and the filtrate was evaporated to dryness to obtain 0.914 g of cis 4-thiocyanatomethyl-3-amino-2-oxo-azetidine hydrochloride.

Step D: Racemate of syn isomer of cis 4-thiocyanatomethyl-3-[2-(2-tritylamino-4-thiazolyl)-2-methoxyimino-acetamido]-2-oxo-azetidine 1 ml of triethylamine and then 1.38 g of tosyl chloride were added to a suspension of 3.19 g of the syn isomer of 2-(2-tritylamino-4-thiazolyl)-2-methoxyimino-acetic acid in 50 ml of methylene chloride and the mixture was stirred at room temperature for 40 minutes. A solution of 1.162 g of the product of Step C in 40 ml of methylene chloride and 2 ml of trietylamine were added to the mixture over 5 minutes and the mixture was stirred for 4 hours, was washed with water, then with water containing 4 ml of N hydrochloric acid, dried and evaporated to dryness. The residue was dissolved in ethyl acetate and the solution was iced and vacuum filtered. The product was washed with methanol and dried to obtain 0.709 g of racemate of syn isomer of cis 4-thiocyanatomethyl-3-[2-(2-tritylamino-4-thiazolyl)-2-methoxyimino-acetamido]-2-oxo-azetidine. The mother liquors were evaporated to dryness and the residue was chromatographed over silica gel. Elution with a 93-7 chloroform-methanol mixture yielded another 1.069 g of the said product.

Step E: Racemate of the syn isomer of cis 4-thiocyanatomethyl-3-[2-(2-amino-4-thiazolyl)-2-methoxyimino-acetamido]-2-oxo-azetidine-1-sulfonic acid A mixture of 1.7 g of the product of Step D, 12 ml of dimethylformamide and 1.16 g of pyridine sulfan was stirred at 20° C. for 90 hours and was poured into ether with stirring. The precipitate was taken up in methanol and the mixture was cooled and vacuum filtered to obtain 2 crops of 0.544 g of the pyridinium salt of the sulfonic acid. A mixture of 0.42 g of the said salt in 4 ml of formic acid containing 33% of water was heated at 60° C. with stirring for 20 minutes and the mixture was cooled to 20° C. 40 ml of ether were added to the mixture which was then stirred at 0° to 5° C. for one hour and was vacuum filtered. The product was rinsed with ether and triturated with aqueous 0.1N sodium bicarbonate solution. The mixture was filtered and the filtrate was adjusted to a pH of 2 by addition of N hydrochloric acid. The mixture was cooled and vacuum filtered and the crystals were washed with water and dried to obtain 0.237 g of racemate of the syn isomer of cis 4-thiocyanatomethyl-3-[2-(2-amino-4-thiazolyl)-2-methoxyimino-acetamido]-2-oxo-azetidine-1-sulfonic acid melting at 265° C. (decomposition).

| Analysis: $C_{11}H_{12}N_6O_6S_3$; molecular weight = 420.54 | | | | |
|---|---|---|---|---|
| | % C | % H | % N | % S |
| Calculated: | 31.42 | 2.88 | 19.99 | 22.88 |
| Found: | 31.2 | 3.2 | 19.7 | 22.6 |

EXAMPLE 8

Racemate of the syn isomer of cis 4-fluoromethyl-3-[2-(2-amino-4-thiazolyl)-2-difluoromethoxyimino-acetamido]-2-oxo-azetidine-1-sulfonic acid

Step A: Racemate of the syn isomer of cis 4-fluoromethyl-3-[2-(2-tritylamino-4-thiazolyl)-2-difluoromethoxyimino-acet-amido]-2-oxo-azetidine 0.339 g of tosyl chloride were added to a mixture of 0.914 g of the syn isomer of 2-(2-tritylamino-4-thiazolyl)-2-difluoromethoxyimino-acetic acid, 7 ml of acetone and 0.25 ml of trietylamine and the mixture was stirred for 50 minutes after which a solution of 0.23 g of cis 4-fluoro-methyl-3-amino-2-oxo-azetidine hydrochloride, 7 ml of methylene chloride and 0.45 ml of triethylamine was added thereto. The mixture was stirred for 90 minutes and was evaporated to dryness. The residue was added to methylene chloride and water and then 3 ml of 10% sodium bicarbonate solution. The mixture was stirred and the decanted aqueous phase was extracted with methylene chloride. The combined organic phases were dried and evaporated to dryness. The residue was taken up in ethanol and the solution was cooled and vacuum filtered. The crystals were rinsed with ethanol, then with ether and dried to obtain 0.537 g of racemate of the syn isomer of cis 4-fluoromethyl-3-[2-(2-tritylamino-4-thiazolyl)-2-difluoro-methoxyimino-acetamido]-2-oxo-azetidine.

Step B: Racemate of the syn isomer of cis 4-fluoromethyl-3-[2-(2-amino-4-thiazolyl)-2-difluoromethoxyimino-acetamido]-2-oxo-azetidine-1-sulfonic acid A solution of the product of Stept A, 0.37 g of pyridine sulfan and 3.7 ml of dimethylformamide was stirred at 20° C. for 72 hours and was poured into 150 ml of ether. The mixture was filtered and the product was washed with ether and was dissolved in ethanol. The solution was stirred and filtered. The crystals were washed with ether and dried to obtain 0.506 g of racemate of the syn isomer of pyridinium cis 4-fluoromethyl-3-[2-(2-tritylamino-4-thiazolyl)-2-difluoro-methoxyimino-acetamido]-2-oxo-azetidine-1-sulfonate.

A mixture of 0.76 g of the said product in 4 ml of formic acid containing 33% water was heated at 60° C. for 15 minutes and was then diluted with water and was filtered. Ethanol was added to the filtrate which was evaporated to dryness. The residue was taken up in a water-ethanol mixture which was then evaporated to dryness. The residue was taken up in water and 2 ml of 10% sodium bicarbonate were added thereto. The mixture was filtered and the pH of the filtrate was adjusted to 2 by addition of 2N hydrochloric acid. The mixture was concentrated and stood for crystallization and was then filtered. The product was washed with water, then with ether and dried to obtain 0.312 g of racemate of the syn isomer of cis 4-fluoromethyl-3-[2-(2-amino-4-thiazolyl)-2-difluoromethoxyimino-acetamido]-2-oxo-azetidine-1-sulfonic acid.

| Analysis: $C_{10}H_{10}O_6N_5S_2F_3$ | | | | |
|---|---|---|---|---|
| | % C | % H | % N | % S | % F |
| Calculated: | 28.78 | 2.41 | 16.78 | 13.66 | 15.36 |
| Found: | 28.9 | 2.5 | 16.6 | 13.4 | 15.3 |

NMR Spectrum (DMSO-90 MHz): Peaks at 4.39 and 4.94 ppm (hydrogens of —CH$_2$F); at 5.21–5.26–5.3 ppm and 5.35 ppm (3-hydrogen-cis); at 6.38–7.15 ppm and 7.93 ppm (hydrogen of —CHF$_2$); at 7.01 ppm (5-hydrogen of thiazolyl); at 9.66 and 9.76 ppm (—CONH hydrogen).

IR Spectrum (chloroform): Absorption at 1770 cm$^{-1}$ (lactam carbonyl); at 1675 cm$^{-1}$ (amide); at 1640 cm$^{-1}$ (amide II); at 1585 cm$^{-1}$ (conjugated system); at 1530 cm$^{-1}$ (thiazole); at 1280–1270 cm$^{-1}$ (—SO$_3$H); and at 1052 cm$^{-1}$

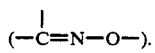

(—C=N—O—).

EXAMPLE 9

Racemate of the syn isomer of cis 4-fluoromethyl-3-[2-(2-amino-4-thiazolyl)-2-hydroxyimino-acetamido]-2-oxo-azetidine-1-sulfonic acid Step A: Racemate of the syn isomer of cis 4-fluoromethyl-3-[2-(2-tritylamino-4-thiazolyl)-2-trityloxyimino-acetamido]-2-oxo-azetidine 0.228 g of tosyl chloride were added to a mixture of 0.806 g of the syn isomer of 2-(2-tritylamino-4-thiazolyl)-2-trityloxyimino-acetic acid, 5 ml of acetone and 0.17 ml of triethylamine and the mixture was stirred for one hour. A solution of 0.155 g of 4-fluoromethyl-3-amino-2-oxo-azetidine hydrochloride in 5 ml of methylene chloride and 0.31 ml of triethylamine was added to the mixture which was stirred for 20 minutes and added to methylene chloride. The mixture was stirred for 90 minutes and was evaporated to dryness. The residue was added to methylene chloride and water with stirring and the decanted organic phase was dried and evaporated to dryness. The residue was chromatographed over silica gel and was eluted with ether to obtain 0.598 g of racemate of the syn isomer of cis 4-fluoromethyl-3-[2-(2-tritylamino-4-thiazolyl)-2-trityloxyimino-acetamido]-2-oxo-azetidine.

Step B: Racemate of the syn isomer of cis 4-fluoromethyl-3-[2-(2-amino-4-thiazolyl)-2-hydroxyimino-acetamido]-2-oxo-azetidine-1-sulfonic acid Using the procedure of Step B of Example 4, the product of Step A was reacted to obtain racemate of the syn isomer of cis 4-fluoromethyl-3-[2-(2-amino-4-thiazolyl)-2-hydroxyimino-acetamido]-2-oxo-azetidine-1-sulfonic acid.

EXAMPLE 10

Optically active cis 3-phthalimido-4-chloromethyl-2-oxo-azetidine

Step A: Optically active cis N-(1-phenyl)-ethyl-3-phthalimido-4-chloromethyl-2-oxo-azetidine 2.55 ml of (+) (1-phenyl)-ethylamine were added with stirring at 0° to 5° C. to a solution of 2.5 ml of aqueous 50% chloroacetaldehyde hydrate in 50 ml of water and the mixture was stirred for 6 minutes and was vacuum filtered. The product was rinsed with water and was taken up in a chloroform-methylene chloride mixture. The solution was dried, cooled under an inert gas to −50° C. and a solution of 4.5 g of phthalimidoacetyl chloride in 25 ml of methylene chloride and a solution of 2.74 ml of triethylamine in 20 ml of methylene chloride were simultaneously and slowly added to the mixture. The temperature was allowed to rise to room temperature and the mixture was stirred for 2½ hours and was poured into a mixture of water and sodium bicarbonate. The mixture was extracted with chloroform and the organic phase was dried and evaporated to dryness. Thr residue was taken up in ethanol and the solution was filtered. The filter was washed with a methylene chloride-ethanol mixture and the filtrate was treated with activated carbon, concentrated and allowed to crystallize to obtain 2 crops of 1.364 g of crystals. The mother liquors were chromatographed over silica gel and eluted with and 8-2 chloroform-ethyl acetate mixture to obtain 1.58 g for a total yield of 2.944 g of optically active cis N-(1-phenyl)-ethyl-3-phthalimido-4-chloromethyl-2-oxo-azetidine which was a sole diastereoisomer.

Step B: Optically active cis 3-phthalimido-4-chloromethyl-2-oxo-azetidine

A mixture of 0.3 g of the product of Step A in 2 ml of acetonitrile was heated at 90° to 95° C. with stirring and a solution of 0.502 g of ammonium persulfate in 2 ml of water was slowly added thereto. The mixture was stirred for 105 minutes and was then poured into water. The mixture was extracted with ethyl acetate and the organic phase was washed with aqueous sodium thiosulfate, dried and evaporated to dryness to obtain 0.058 g of optically active cis 3-phthalimido-4-chloromethyl-2-oxo-azetidine with a specific rotation of $[\alpha]_D^{20} = +10.5° \pm 1°$ (chloroform) and melting at 172° C. The product could be reacted by the procedure of Examples 1,2,4 or 5 to obtain the corresponding optically active isomers of formula I.

EXAMPLE 11

(3S,4S)ΔZ 4-fluoromethyl-3-[2-(2-amino-4-thiazolyl)-2-methoxyimino-acetamido]-2-oxo-azetidine-1-sulfonic acid Step A: 4-fluoromethyl-3-phthalimido-2-oxo-1-(1-phenylethyl)-azetidine A mixture of 96.6 ml of an aqueous solution of 0.797M per liter of fluoroacetaldehyde hydrate, 100 ml of iced aqueous saturated sodium chloride solution and 9.8 ml of R(+) phenethylamine was stirred for 10 minutes and was then extracted with 192 ml of chloroform. The organic phase was dried and cooled to −70° C. under an inert atmosphere and then a solution of 16.8 g of phthalimidoacetyl chloride in 77 ml of chloroform and a solution of 7.8 g of triethylamine in 77 ml of chloroform were simultaneously added to the mixture over 15 minutes at −50°±2° C. The mixture was heated to room temperature and was allowed to stand for one hour after which 46 ml of an aqueous 10% sodium bicarbonate solution were added thereto. Then, 77 ml of water were added and the mixture was vigorously stirred. The decanted aqueous phase was extracted with methylene chloride and the combined organic phases were washed with water, dried and evaporated to dryness under reduced pressure. The residue was chromatographed over silica gel and eluted with a 95-5 benzene-acetone mixture to obtain 10.3 g of the 3S,4S isomer of 4-fluoromethyl-3-phthalimido-2-oxo-1-(1-phenyl-ethyl)-azetidine with a specific rotation of $[\alpha]_D^{20} = -29° \pm 1.5°$ (c=1% in methanol) and 2.5 g of the corresponding 3R,4R isomer with a specific rotation of $[\alpha]_D^{20} = 50° + 1.5°$ (c=1% in chloroform).

| Analysis: $C_{20}H_{17}O_3N_2F$; molecular weight = 352.37 | | | | |
| --- | --- | --- | --- | --- |
| | % C | % H | % N | % F |
| Calculated: | 68.2 | 4.86 | 7.95 | 5.40 |
| Found: | | | | |
| 3S,4S isomer | 68.4 | 4.9 | 8.0 | 5.3 |
| 3R,4R isomer | 67.1 | 4.8 | 7.4 | 5.1 |

Step B: (3S,4S) 4-fluoromethyl-3-phthalimido-2-oxo-1-azetidine

A mixture of 9.8 g of the (3S,4S) isomer of Step A, 150 ml of acetonitrile and 96.5 ml of water was heated to reflux and a solution of 15.9 g of ammonium peroxydisulfate in 39 ml of water was added thereto over 15 minutes. The mixture was refluxed for 90 minutes and then cooled and saturated with sodium chloride. The mixture was extracted with ethyl acetate and the organic phase was washed with 100 ml of aqueous saturated sodium chloride solution containing 20 g of sodium thiosulfate, dried and evaporated to dryness under reduced pressure. The residue was chromatographed over silica gel and eluted with a 3-1 methylene chloride-ethyl acetate mixture. The product was crystallized from ether to obtain 2.33 g of (3S,4S) 4-fluoromethyl-3-phthalimido-2-oxo-1-azetidine with a specific rotation of $[\alpha]_D^{20} = +7° \pm 1\%$ (c=1% in methanol) and melting at 160°-162° C.

Step C: (3S,4S) 4-fluoromethyl-3-amino-2-oxo-azetidine hydrochloride 26 ml of a solution of 1 ml of hydrazine hydrate in 50 ml of dioxane were added over 20 minutes to a mixture of 2.3 g of the product of Step B and 2.3 ml of dioxane and after standing at room temperature for 45 minutes, 9.3 ml of N hydrochloric acid were added thereto. The mixture was stirred under an inert atmosphere at room temperature for 16 hours and was evaporated to dryness under reduced pressure. The residue was taken up in 100% ethanol and the solution was evaporated to dryness. The residue was dissolved in a minimum of methanol and ethanol was added there-to after which the mixture was evaporated to dryness. The residue was dissolved in a minimum of refluxing methanol and the solution was iced and vacuum filtered. The product was rinsed with cold methanol and with ether to obtain 1.10 g of (3S,4S) 4-fluoromethyl-2-amino-2-oxo-azetidine hydrochloride melting at >220° C. (decomposition) and having a specific rotation of $[\alpha]_D^{20} = -25.5° \pm 1°$ (c=1% in methanol).

Step D: (3S,4S) ΔZ 4-fluoromethyl-3-[2-(2-tritylamino-4-thiazolyl)-2-methoxyimino-acetamido]-2-oxo-1-azetidine A mixture of 2.85 g of 2-tritylamino-4-thiazolyl-2-methoxyimino-acetic acid, 0.92 ml of triethylamine, 33 ml of acetone and 1.23 g of tosyl chloride was stirred for 40 minutes and then a solution of 0.95 g of the product of Step C, 1.85 ml of triethylamine and 33 ml of methylene chloride was added thereto. The mixture was evaporated to dryness and the residue was taken up in ethyl acetate. The organic solution was washed with water, with aqueous 10% sodium bicarbonate solution, dried and evaporated to dryness under reduced pressure. The residue was chromatographed over silica gel and eluted with a 8-2 methylene chloride-acetone mixture. The product was crystallized from ethyl acetate to obtain 1.36 g of (3S,4S)ΔZ 4-fluoromethyl-3-[2-(2-tritylamino-4-thiazolyl)-2-methoxyimino-acetamido]-2-oxo-1-azetidine melting at >220° C. (decomposition) and having a specific rotation of $[\alpha]_D^{20} = -2° \pm 0.5°$ (c=1% in dimethylformamide).

| Analysis: $C_{29}H_{26}O_3N_5SF$; molecular weight = .543.62 | | | | | |
| --- | --- | --- | --- | --- | --- |
| | % C | % H | % N | % S | % F |
| Calculated: | 64.07 | 4.82 | 12.9 | 5.9 | 3.49 |
| Found: | 63.7 | 4.9 | 12.6 | 5.9 | 3.3 |

Step E: (3S,4S)ΔZ 4-fluoromethyl-3-[2-(2-amino-4-thiazolyl)-2-methoxyiminoacetamido]-2-oxo-1-azetidine-1-sulfonic acid A mixture of 660 mg of the product of Step D, 600 mg of a complex of pyridine and SO3 and 5 ml of dimethylformamide were stirred under an inert atmosphere for 90 hours and was evaporated to dryness under reduced pressure. 600 mg of a pyridine-SO3 complex and 3 ml of dimethylformamide were added to the residue and themixture was stirred for 48 hours and poured into 250 ml of ether. The decanted aqueous phase was added to acetone and the mixture was filtered to remove excess complex. The filtrate was evaporated to dryness and the residue was dissolved in methanol and chromatographed under pressure over silica gel. Methanol was used as the eluate and the eluate was evaporated to dryness. The residue was taken up in 3 ml of formic acid containing 33% of water and the mixture was heated at 50° C. with stirring for 30 minutes and was then filtered. Ethanol was added to the filtrate and the mixture was evaporated to dryness. The process was repeated several times to the ppoint of crystallization. The mixture was vacuum filtered and the 150 mg of product were purified by passage through Mitsubishi resin HP20 to obtain 55 mg of (3S,4S) ΔZ 4-fluoromethyl-3-[2-(2-amino-4-thiazolyl)-2-methoxyimino-acetamido]-2-oxo-1-azetidine-1-sulfonic acid melting at >220° C. (decomposition) and having a specific rotation of $[\alpha]_D^{20} = -14.5° \pm 2°$ (c=0.3% in water).

| Analysis: $C_4H_8ON_2ClF$; molecular weight = 154.57 | | | | | |
| --- | --- | --- | --- | --- | --- |
| | % C | % H | % N | % Cl | % F |
| Calculated: | 31.08 | 5.22 | 18.12 | 22.24 | 12.29 |
| Found: | 32.1 | 5.2 | 17.0 | 20.8 | 11.4 |

| Analysis: $C_{10}H_{12}O_6N_5S_2F$; molecular weight = 381.36 | | | | | |
| --- | --- | --- | --- | --- | --- |
| | % C | % H | % N | % S | % F |
| Calculated: | 31.5 | 3.17 | 18.35 | 16.8 | 4.98 |
| Found: | 31.6 | 3.1 | 17.9 | 16.0 | 4.8 |

EXAMPLE 12

An injectable solution was prepared by dissolving 500 mg of the racemate of the syn isomer of cis 4-fluoromethyl-3-[2-(2-amino-4-thiazolyl)-2-methoxyimino-acetamido]-2-oxo-azetidine-1-sulfonic acid or (3S,4S) ΔZ 4-fluoromethyl-3-[2-(2-amino-4-thiazolyl)-2-methoxyimino-acetamido]-2-oxo-azetidine-1-sulfonic acid and sufficient sterile aqueous excipient for a volume of 5 ml. Gelules were prepared containing 250 mg of the racemate of the syn isomer of cis 4-fluoro-methyl-3-[2-(2-amino-4-thiazolyl)-2-methoxyiminoacetamido]-2-oxo-azetidine-1-sulfonic acid or (3S,4S) ΔZ 4-fluoromethyl-3-[2-(2-amino-4-thiazolyl)-2-methoxyimino-acetamido]-2-oxo-azetidine-1-sulfonic acid and sufficient excipient for a capsule weighing 400 mg.

PHARMACOLOGICAL DATA

A. Activity in Vitro-Method of Dilutions in Liquid Medium

A series of tubes was prepared in which the same amount of sterile nutritive medium was distributed and there was distributed in each tube increasing amounts of the test product. Then, each tube was inoculated with a bacterial strain and after incubation for twenty-four or forty-eight hours in an oven at 37° C., the inhibition of the growth was evaluated by trans-illumination to determine the minimum inhibiting concentrations (M.I.C.), expressed in μg/ml. The determined results are reported in the following Tables.

| Product of Example 1 | | |
|---|---|---|
| | M.I.C. in μg/ml | |
| STRAINS | 24 Hr. | 48 Hr. |
| *Escherichia Coli* Sensitive to Tetracycline 7624 | 1.25 | 1.25 |
| *Escherichia Coli* Resistant to Tetracycline AT CC 11 303 | 0.16 | 0.16 |
| *Enterobacter Cloacae* 681 | 2.5 | 2.5 |
| *Escherichia Coli* Resistant to Gentamycine Tobramycine R55 123 D | 0.62 | 0.62 |
| *Klebsiella Pneumoniae* Exp. 52145 | 1.25 | 2.5 |
| *Klebsiella Pneumoniae* 2536 Resistant Gentamycine | 2.5 | 2.5 |
| *Proteus mirabilis* (indol −) A 235 | 0.16 | 0.16 |
| *Proteus vulgaris* (indol +) A 232 | 0.08 | 0.08 |
| *Salmonella typhimurium* 420 | 1.25 | 1.25 |
| Providencia Du 48 | 0.62 | 0.62 |
| Serratia Resistant to Gentamycine 2 532 | 5 | 5 |

| | M.I.C. in μg/ml | | | |
|---|---|---|---|---|
| | Product of example 3 | | Product of example 4 | |
| STRAINS | 24 Hr. | 48 Hr. | 24 Hr. | 48 Hr. |
| *Escherichia Coli* Sensitive to Tetracycline 7624 | 1.2 | 1.2 | 0.6 | 0.6 |
| *Escherichia Coli* Resistant to Tetracyline AT CC 11 303 | 0.6 | 0.6 | 0.6 | 0.6 |
| *Escherichia Coli* Resistant to Gentamycine Tobramycine R 55 123 D | 1.2 | 1.2 | 0.6 | 0.6 |
| *Klebsiella Pneumoniae* Exp. 52 145 | 5 | 10 | 5 | 5 |
| *Klebsiella Pneumoniae* 2 536 Resistant Gentamycine | 2.5 | 2.5 | 2.5 | 2.5 |
| *Proteus mirabilis* (indol −) A 235 | 0.6 | 0.6 | 0.6 | 1.2 |
| *Proteus vulgaris* (indol +) A 232 | 1.2 | 1.2 | 0.6 | 0.6 |
| *Salmonella typhimurium* 420 | 2.5 | 5 | 1.2 | 2.5 |
| Providencia Du 48 | 2.5 | 2.5 | 0.6 | 1.2 |
| Serratia Resistant to Gentamycine 2 532 | 2.5 | 5 | 5 | 5 |

| Product of Example 5 | | |
|---|---|---|
| | M.I.C. in μg/ml | |
| Strains | 24 H | 48 H |
| *Pseudomonas aeruginosa* 1771 m | 0.6 | 1.2 |
| *Escherichia coli* UC 1894 | ≦0.04 | ≦0.04 |
| *Escherichia coli* 0 78 | 0.15 | 0.15 |
| *Escherichia coli* T E M | 0.15 | 0.15 |
| *Escherichia coli* 1507 E | 0.15 | 0.15 |
| *Escherichia coli* DC 0 | 0.3 | 0.3 |
| *Escherichia coli* DC 2 | 0.15 | 0.3 |
| *Salmonella typhimurium* MZ 11 | 0.08 | 0.08 |
| *Klebsiella pneumoniae* Exp. 52 145 | 0.3 | 0.3 |
| *Klebsiella aerogenes* 1082 E | 5 | 5 |
| *Klebsiella aerogenes* 1522 E | 0.15 | 0.15 |
| *Enterobacter cloacae* 1321 E | 0.08 | 0.08 |
| Serratia RG 2532 | 0.06 | 1.2 |
| *Proteus mirabilis* (indol −) A 235 | 0.08 | 0.08 |
| *Proteus vulgaris* (indol +) A 232 | ≦0.04 | ≦0.04 |
| Providencia Du 48 | 0.3 | 0.3 |

| Product of Example 6 | | |
|---|---|---|
| | M.I.C. in μg/ml | |
| Strain | 24 H | 48 H |
| *Pseudomonas aeruginosa* 1771 m | 0.3 | 0.6 |
| *Escherichia coli* UC 1894 | 0.08 | 0.08 |
| *Escherichia coli* 0 78 | 0.3 | 0.3 |
| *Escherichia coli* T E M | 0.6 | 0.6 |
| *Escherichia coli* 1507 E | 0.6 | 0.6 |
| *Escherichia coli* DC 0 | 0.6 | 0.6 |
| *Escherichia coli* DC 2 | 0.3 | 0.3 |
| *Salmonella typhimurium* MZ 11 | 0.6 | 0.6 |
| *Klebsiella pneumoniae* Exp. 52 145 | 0.6 | 0.6 |
| *Klebsiella aerogenes* 1082 E | 0.6 | 0.6 |
| *Klebseilla aerogenes* 1522 E | 0.3 | 0.3 |
| *Enterobacter cloacae* 1321 E | 0.3 | 0.3 |
| Serratia RG 2 532 | 0.3 | 0.3 |
| *Proteus mirabilis* (indol −) A 235 | ≦0.04 | ≦0.04 |
| *Proteus vulgaris* (indol +) A 232 | ≦0.04 | ≦0.04 |
| Providencia Du 48 | 0.15 | 0.15 |

| Product of Example 8 | | |
| --- | --- | --- |
| | M.I.C. µg/ml | |
| Strains | 24 H | 48 H |
| Escherichia coli UC 1894 | ≦0.04 | ≦0.08 |
| Escherichia coli 0 78 | 0.08 | 0.08 |
| Escherichia coli T E M | 0.15 | 0.15 |
| Escherichia coli 1507 E | ≦0.04 | ≦0.04 |
| Escherichia coli DC 0 | 0.08 | 0.08 |
| Escherichia coli DC 2 | ≦0.04 | ≦0.04 |
| Salmonella typhimurium MZ 11 | 0.08 | 0.08 |
| Klebsiella pneumoniae Exp. 52 145 | 0.3 | 0.3 |
| Klebseilla aerogenes 1522 E | 0.08 | 0.08 |
| Enterobacter cloacae 1321 E | 0.08 | 0.08 |
| Serratia RG 2532 | 0.6 | 0.6 |
| Proteus mirabilis (indol —) A 235 | ≦0.04 | ≦0.04 |
| Proteus vulgaris (indol +) A 232 | ≦0.04 | ≦0.04 |
| Providencia Du 48 | 0.3 | 0.3 |

| PRODUCT OF EXAMPLE 11 | |
| --- | --- |
| Souches | CM I en 24 H µg/ml |
| Pseudomonas aeruginosa 1771 m | 0.6 |
| Escherichia coli UC 1894 | ≦0.04 |
| Escherichia coli 0 78 | 0.08 |
| Escherichia coli T E M | 0.08 |
| Escherichia coli 1507 E | 0.08 |
| Escherichia coli DC 0 | 0.15 |
| Escherichia coli DC 2 | 0.15 |
| Salmonella typhimurium MZ 11 | ≦0.04 |
| Klebsiella pneumoniae Exp. 52 145 | 0.08 |
| Klebsiella aerogenes 1082 E | 10 |
| Klebsiella aerogenes 1522 E | 0.08 |
| Enterobacter cloacae 1321 E | 0.08 |
| Serratia RG 2532 | 2.5 |
| Proteus mirabilis (indol —) A 235 | 0.15 |
| Proteus vulgaris (indol +) A 232 | ≦0.04 |
| Providencia Du 48 | 0.3 |

Various modifications of the products and processes of the invention may be made without departing from the spirit or scope thereof and it is to be understood that the invention is intended to be limited only as defined in the appended claims.

What we claim is:

1. A compound selected from the group consisting of syn isomers of racemates and optical isomers of 3-amino-2-oxo-azetidine-1-sulfonic acids of the formula

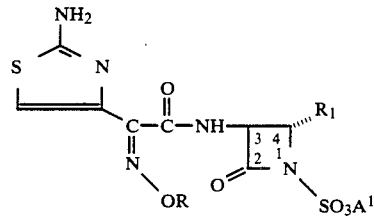

wherein R is difluoromethyl, $R_1$ is $-(CH_2)_n-X$, n is an integer from 1 to 4, X is fluorine, and $A^1$ is selected from the group consisting of hydrogen and pharmaceutically acceptable metal cations and their non-toxic, pharmaceutically acceptable acid addition salts, the wavy line indicates the cis form, trans form or cis trans form.

2. A compound of claim 1 of the formula

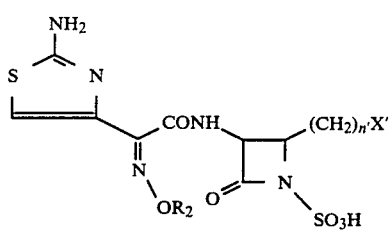

wherein $R_2$ is difluoromethyl, n' is a whole number 1 or 2 and X' is fluoro, in the racemic or optically active form, as well as the non-toxic, pharmaceutically acceptable salts of the said compounds with bases or acids.

3. An antibacterial composition comprising an antibacterically effective amount of at least one compound of claim 1 and a pharmaceutically acceptable excipient.

4. A composition of claim 3 wherein the compound is of the formula

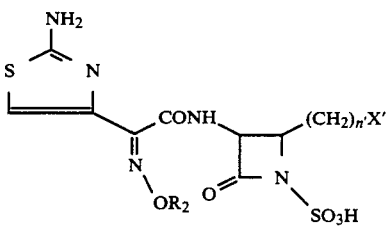

I' wherein $R_2$ is difluoromethtyl, n' is a whole number 1 or 2 and X' is fluoro, in the racemic or optically active form, as well as the non-toxic, pharmaceutically acceptable salts of the said compounds with bases or acids.

5. A method of combatting bacterial infections in warm-blooded animals comprising administering to warm-blooded animals an antibacterially effective amount of at least one compound of claim 1.

6. A method of claim 5 wherein the compound is of the formula

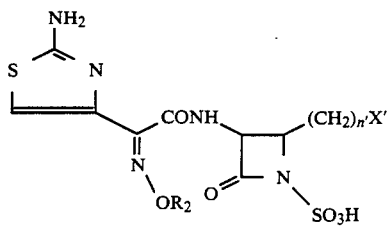

wherein $R_2$ is difluoromethyl, n' is a whole number 1 or 2 and X' is fluoro in the racemic or optically active form, as well as the non-toxic, pharmaceutically acceptable salts of the said compounds with bases or acids.

7. A Compound of claim 1 selected from the group consisting of the racemate or optically active isomer of the syn isomer of cis 4-fluoromethyl-3-[2-(2-amino-4-thiazolyl)-2-difluoro methoxy-imino-acetamido]2-oxo-azetidine-1-sulfonic acid and its pharmaceutically acceptable salts.

8. A compound of claim 1 when n is 1.

9. A composition of claim 3 wherein the compound is selected from the group consisting of the racemate or optically active isomer of the syn isomer of cis 4-fluoromethyl-3-[2-(2-amino-4-thiazolyl)-2-difluoro methoxy-iminoacetamido]-2-oxo-azetidine-1-sulfonic acid and its pharmaceutically acceptable salts.

10. A method of claim 6 wherein n' is 1.

11. A method of claim 5 wherein the compound is selected from the group consisting of the racemate or optical isomer of the syn isomer of cis 4-fluoromethyl-3-[2-(2-amino-4-thiazolyl)-2-difluoromethoxy-iminoacetamido]-2-oxo-azetidine-1-sulfonic acid and its pharmaceutically acceptable salts.

12. A composition of claim 3 wherein n' is 1.

* * * * *